United States Patent
Kushner et al.

(10) Patent No.: US 8,063,249 B1
(45) Date of Patent: Nov. 22, 2011

(54) SUBSTITUTED TRIPHENYL BUTENES

(75) Inventors: Peter Kushner, San Francisco, CA (US); Cyrus Harmon, Berkeley, CA (US); David Myles, Berkeley, CA (US)

(73) Assignee: Olema Pharmaceuticals, Inc., San Francisco, CA (US)

( * ) Notice: Subject to any disclaimer, the term of this patent is extended or adjusted under 35 U.S.C. 154(b) by 0 days.

(21) Appl. No.: 12/429,128

(22) Filed: Apr. 23, 2009

Related U.S. Application Data

(60) Provisional application No. 61/048,026, filed on Apr. 25, 2008, provisional application No. 61/076,561, filed on Jun. 27, 2008.

(51) Int. Cl.
- C07C 215/46 (2006.01)
- C07C 217/54 (2006.01)
- A61K 31/133 (2006.01)

(52) U.S. Cl. .......................... 564/324; 514/648
(58) Field of Classification Search .................. None
See application file for complete search history.

(56) References Cited

U.S. PATENT DOCUMENTS

| | | | |
|---|---|---|---|
| 4,252,951 A * | 2/1981 | Jackson et al. | 540/220 |
| 4,659,516 A | 4/1987 | Bowler et al. | |
| 4,760,061 A | 7/1988 | Edwards et al. | |
| 2003/0138432 A1 | 7/2003 | Glazier | |
| 2005/0101583 A1 | 5/2005 | Stevenson et al. | |

FOREIGN PATENT DOCUMENTS
WO    WO 90/10638    9/1990

OTHER PUBLICATIONS

Agouridas et al., Bioorganic & Medicinal Chemistry (2006), 14, p. 7531-7538.*
Braga et al., Chem. Commun. (2005), 29, p. 3635-3645.*
Burger's Medicinal Chemistry and Drug Discovery $5^{th}$ ed., vol. I, (1995), Manfred E. Wolff ed., John Wiley & Sons, NY, p. 975-977.*
Modern Pharmaceuticals $3^{rd}$ ed., (1996), Gilbert S. Banker et al. ed., Marcel Dekker, Inc. NY, p. 596.*
Weatherman et al., "Synthesis and Characterization of Bioactive Tamoxifen-Conjugated Polymers," Biomacromolecules, 8, pp. 3608-3612, 2007.

* cited by examiner

*Primary Examiner* — Brian J Davis
(74) *Attorney, Agent, or Firm* — Margaret B. Brivanlou; King & Spalding LLP

(57) ABSTRACT

The present invention is directed to compounds, compositions thereof, and the use of the compounds and compositions for the treatment and prevention of breast cancer. In one embodiment, the present invention relates to the use of a substituted triphenyl butene or prodrug thereof for the treatment of breast cancer in mono-therapy or in combination therapy, or for a reduction in the recurrence rate of previously-treated breast cancer.

17 Claims, 9 Drawing Sheets

Notes:
1. R groups have been selected to compliment the mildly acidic cleavage conditions of the BOC protecting group used in Route II
2. Benzyloxy carbonyls (CBZ) are cleaved reductively and nucleophilically
3. Florinylmethyl oxycarbonyls (FMOC) are cleaved under basic conditions
4. 4-OMeBOC carbamates are cleaved under acidic or oxidative conditions Methyl (R = H) or ethylene carbonates Sulfamate ester phosphonooxylmethyl (R = H) or ethyl (R = Me)

SUBSTITUTED TRIPHENYL BUTENES

This application claims priority to U.S. provisional patent applications 61/048,026, filed Apr. 25, 2008, and 61/076,561, filed Jun. 27, 2008, and the entire contents of each of the priority applications are incorporated by reference.

1. FIELD OF THE INVENTION

The present invention is directed to compounds, compositions thereof, and the use of the compounds and compositions for the treatment and prevention of breast cancer. In one embodiment, the present invention relates to the use of a substituted triphenyl butene or a prodrug thereof for the treatment of breast cancer in mono-therapy or in combination therapy, or for a reduction in the recurrence rate of previously-treated breast cancer. In an alternative embodiment, intermediates are presented for the synthesis of compounds and compositions for the treatment and prevention of breast cancer.

2. BACKGROUND OF THE INVENTION

Among women in the U.S., breast cancer is the most common cancer and the second-most common cause of cancer death. Estrogen Receptor (ER)-positive breast cancer is treated with agents designed to block the pro-proliferative action of the estrogen receptor. One such agent is the antiestrogen tamoxifen.

Tamoxifen itself binds very poorly to the ER. However, when activated by metabolic action, tamoxifen gives rise to derivatives that bind very tightly to the ER and put it in an inactive state that prevents it from modulating transcription of pro-proliferative genes. The tamoxifen is activated to inhibit ER action by metabolizing enzymes that convert the tamoxifen to 4-hydroxy tamoxifen (4-OHT) or to 4-hydroxy N-desmethyl tamoxifen (also known as endoxifen). These later compounds bind with high affinity to the ER, with binding constants roughly equal to that of estradiol. See Jordan, V. C., "New insights into the metabolism of tamoxifen and its role in the treatment and prevention of breast cancer," Steroids, vol. 72, issue 13, pp. 829-842, November 2007.

Some women have defects in the activating enzymes of tamoxifen metabolism, especially the cytochrome p450 enzyme Cyp2D6, resulting in lowered levels of active tamoxifen metabolites in their circulation. See Lim, H.-S. et al., "Clinical Implications of CYP2D6 Genotypes Predictive of Tamoxifen Pharmacokinetics in Metastatic Breast Cancer," Journal of Clinical Oncology, vol. 25, no. 25, pp. 3837-3845, Sep. 1, 2007; Schroth, W. et al., "Breast Cancer Treatment Outcome With Adjuvant Tamoxifen Relative to Patient CYP2D6 and CYP2C19 Genotypes," Journal of Clinical Oncology, vol. 25, no. 33, pp. 5187-5193, Nov. 20, 2007; and Kiyotani, K. et al., "Impact of CYP2D6*10 on recurrence-free survival in breast cancer patients receiving adjuvant tamoxifen therapy," Cancer Science, Online Early Articles, pp. 1-5, published online Feb. 24, 2008. Women with such defects have a poorer response to tamoxifen therapy and reduced tumor-free survival. In contrast, women with super-fast metabolism of tamoxifen and increased endoxifen levels have a superior clinical response to tamoxifen. See Schroth, W. et al., "Breast Cancer Treatment Outcome With Adjuvant Tamoxifen Relative to Patient CYP2D6 and CYP2C19 Genotypes," Journal of Clinical Oncology, vol. 25, no. 33, pp. 5187-5193, Nov. 20, 2007. In addition to these genetic factors, it is also known that certain drugs, especially selective serotonin reuptake inhibitors (SSRIs) such as PAXIL®, also interfere with Cyp2d6 activity including the conversion of tamoxifen to active metabolites (discussed in Jordan, V. C., "New insights into the metabolism of tamoxifen and its role in the treatment and prevention of breast cancer," Steroids, vol. 72, issue 13, pp. 829-842, November 2007).

The activity of tamoxifen, 4-hydroxytamoxifen, and endoxifen are affected by their rates of processing in the body. Endoxifen and 4-hydroxytamoxifen have hydroxy groups that are reported to be substrates for O-glucuronidation by two UGTs: 1A8 and 1A10. See Sun, D. et al., "Glucuronidation of Active Tamoxifen Metabolites by the Human UDP Glucuronosyltransferases," Drug Metabolism and Disposition, vol. 35, no. 11, pp. 2006-2014, November 2007. These enzymes are present in both the gut and liver as well as other extrahepatic tissues and may possibly inactivate endoxifen by O-linked glucuronidation at the hydroxyl group. For example, it has been reported that glucuronated endoxifen can no longer bind to the ER (Zheng, Y. et al., "Elimination of Antiestrogenic Effects of Active Tamoxifen Metabolites by Glucuronidation," Drug Metabolism and Disposition, vol. 35, no. 10, pp. 1942-1948, October 2007). Thus, the current treatment of breast cancer with tamoxifen has an uneven effect on different patients due in part to variations in the manner in which patients metabolize tamoxifen or its metabolite endoxifen.

3. SUMMARY OF THE INVENTION

To overcome these and other problems with breast cancer therapy, the present invention is directed to substituted triphenyl butenes or related compounds with improved clinical outcome. Compounds according to the invention may result in improved outcomes for patients non-responsive to tamoxifen therapy due to the cytochrome p450 enzyme Cyp2D6. Compounds according to the invention may have improved bioavailability in that they are no longer substrates for UGTs in the gut, or may be more readily absorbed than tamoxifen or endoxifen. Prodrugs according to the invention may include, for example, phosphate compounds in which the hydroxyl moiety is modified to a phosphate, where the phosphate may lead to more efficient absorption when it is converted to an active agent at high concentration at the apical cell surface. These and other advantages are more fully described below.

The present invention is directed to compounds, compositions thereof, and the use of the compounds and compositions for the treatment and prevention of breast cancer. Compounds according to the invention are substituted triphenyl butenes, and may be considered in the same anti-cancer category of compounds as tamoxifen, endoxifen, and related compounds. The compounds may be used for the treatment of breast cancer, or for a reduction in the recurrence rate or severity of previously-treated breast cancer. In an alternative embodiment, intermediate compounds according to the invention are used for the synthesis of an anti-cancer agent.

According to one embodiment, the invention is a compound of formula I or formula II:

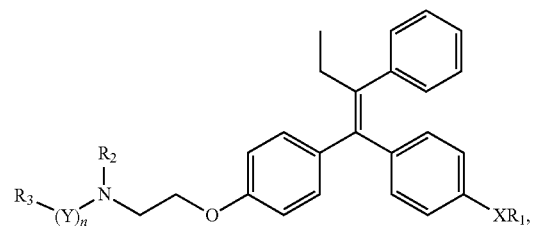

-continued

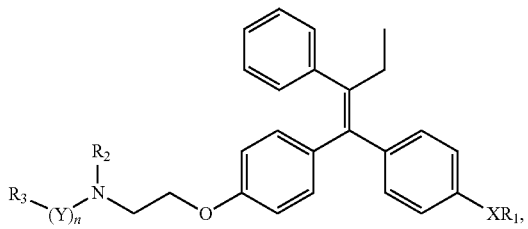

II and pharmaceutically acceptable salts thereof, wherein X is H, O, or S; $R_1$ is H or a prodrug moiety, or not present when X is H; $R_2$ is H, $CH_3$, a lower alkyl group, a divalent cyclic alkyl group forming a quaternary ammonium, or a prodrug moiety; $R_3$ is a polyfluoro alkyl group; n is an integer from 0 to 10; and Y is a linker. While the compounds of Formula I and II are drawn with a specific orientation around the double bond, both E and Z configurations around the double bond are encompassed by the invention, individually as compounds and together in equimolar or non-equimolar mixtures in compositions.

According to another embodiment, the invention is a compound as described above, wherein X is O, and $R_1$ is independently selected from the group consisting of esters, carbonate esters, phosphate esters, diphosphate esters, triphosphate esters, ethers, and alpha-acyloxyalkyl ethers.

In an alternate embodiment, the invention is a compound as described above, wherein $R_2$ is independently selected from amides and carbamates, N-acyloxyalkyl derivatives, N-acylalkoxy carbonyl derivatives, beta-aminoketones, (oxodioxolenyl)methyl derivatives, N-Mannich bases, imines (Schiff bases), enamines and enaminones, azo compounds, lactonization systems, THTT, redox systems, and PEG.

According to another embodiment, the invention is a compound as described above, wherein $R_3$ is selected from a $C_1$-$C_6$ polyfluoroalkyl group. In one embodiment, $R_3$ is selected from a $C_1$-$C_6$ perfluoroalkyl group. Alternately, the compound contains $R_3$, which is selected from perfluoromethyl and perfluoroethyl.

In one embodiment, Y is —$R_4SR_5$—, —$R_4SOR_5$—, —$R_4SO_2R_5$—, —$R_4OR_5$—, —$R_4NR_2R_5$—, —$R_4NR_2COR_5$—, —$R_4CONR_2R_5$—, —$R_4COR_5$—, —$R_4C(=O)OR_5$—, —$R_4OC(=O)R_5$—, —$R_4POR_5$—, —$R_4OP(=O)(OH)OR_5$—, —$R_4NR_2C(=NR_2)NR_2R_5$—, —$R_4NR_2C(=O)NR_2R_5$—, —$R_4NR_2C(=O)OR_5$—, and —$R_4OC(=O)NR_2R_5$—; wherein $R_2$ is as defined above, and $R_4$ and $R_5$ are independently selected from $C_1$-$C_{10}$ straight-chain, branched, or cyclic alkyl, $C_2$-$C_{10}$ straight-chain, branched, or cyclic alkenyl, $C_2$-$C_{10}$ straight-chain or branched alkynyl, divalent aryl, and divalent heterocyclyl groups. In a preferred embodiment, Y is —$R_4OR_5$— or —$R_4NR_2R_5$—. Preferably, n is an integer from 2 to 4.

According to one embodiment, the invention is a composition comprising a compound according to claim 1 and a pharmaceutically acceptable carrier. For example, the invention may be a composition as described above, wherein the compound is optically active, and wherein the composition further comprises an enantiomer of the compound, and further wherein the compound and its enantiomer are present in an equimolar or non-equimolar ratio. Alternately, the invention is a composition, wherein the physical form of the compound is selected from the group consisting of an anhydrous form, a single crystalline form, a mixture of polymorphic forms, a hydrated form, and mixtures thereof. Also included is a composition comprising a mixture of compounds according to Formulas I or II, or salts thereof, wherein the mixture comprises a compound according to Formula I and a compound according to Formula II, wherein the compounds are E/Z isomers of each other. In one embodiment, the E/Z isomers are present in an equimolar ratio or a non-equimolar ratio.

According to one embodiment, the invention is a method of treating breast cancer in a human in need thereof comprising administering a compound according to formulas I or II, or salts thereof, to a human. The human may be female. Alternately, the female patient is non-responsive to treatment with tamoxifen. Such non-responsiveness may be determined by a method selected from the group consisting of liver enzyme assay, genotyping Cyp2D6 for one or more copies of the *10 allele, detecting the presence, absence, or levels of endoxifen in biological fluids, determining if the patient is taking drugs that interfere with tamoxifen metabolism, and combinations thereof. In a preferred embodiment, non-responsiveness is determined by an assay of Cyp2D6 activity. The method according to the invention may also involve administration of one or more additional active agents.

In one embodiment, the breast cancer is ER-positive. In a preferred embodiment, the dose of compound of Formula I or II, or salt thereof, is bioequivalent to an oral tamoxifen dose of between about 2 to about 40 mg per day.

In one embodiment, the invention is a method of reducing the rate or severity of recurrence of breast cancer in a human previously treated for breast cancer comprising administering a compound according to Formula I or Formula II, or salt thereof, to a human in need thereof.

In one embodiment, compounds according to the above formulas are capable of being metabolized in vivo to endoxifen in one or more steps. Those compounds which are metabolized in vivo to endoxifen may be referred to as endoxifen prodrugs. For example, the compounds may be metabolized through a pathway that does not involve liver enzymes, or does not specifically involve Cyp2D6, such as hydrolysis in the stomach. In one embodiment, the compounds are resistant to glucuronidation at either the O- or N-position. Alternatively, the compounds according to the invention may have improved bioavailability by virtue of improved oral adsorption compared to endoxifen or related compounds.

In one embodiment, the invention encompasses methods of making compounds according to the above formulas. In another aspect, the invention includes compositions comprising a pharmaceutically acceptable carrier and a compound according to the above formula. Such compositions may be pharmaceutical formulations themselves, or may be formulated with additional ingredients at a later time prior to administration to yield the actual pharmaceutical formulation. Compositions according to the invention may have a physical form of the compound selected from the group consisting of an anhydrous form, a single crystalline form, a mixture of polymorphic forms, a hydrated form, and mixtures thereof. Alternatively, the invention encompasses methods of making a medicament comprising the addition of a compound according to the above formula to a pharmaceutically-acceptable carrier. The present invention also provides pharmaceutical compositions comprising or consisting essentially of the compounds described herein, as well as kits comprising the compositions and combinations thereof.

In one embodiment, the invention encompasses methods of treating breast cancer, or of reducing the rate or severity of recurrence of breast cancer in previously-treated breast cancer patients. Treating includes management of, amelioration of symptoms of, and slowing the progression of the condition.

Methods according to the invention comprise administering to a patient in need thereof a therapeutically effective amount of the compound as an active agent. In one embodiment, the breast cancer is estrogen receptor (ER) positive. Treatment may be directed to those patients that will benefit the most from a compound according to the invention as an alternative to tamoxifen. For example, treatment may be directed at human females who are resistant or non-responsive to tamoxifen treatment. Non-responsiveness may be found empirically through dosage with tamoxifen, or it may be inferred through genetic, enzymatic, or other assay of samples from the patient. Alternatively, non-responsiveness to tamoxifen may be a transient or induced condition. For example, non-responsiveness to tamoxifen may be due to administration of one or more drugs for a condition other than breast cancer, such as SSRIs or monoamine oxidase inhibitors used in psychiatric or other types of patients. Non-responsiveness to tamoxifen may be due to inability to convert tamoxifen to endoxifen in vivo, or may be due to resistance by overexpression of HER2/neu by the cancer cells, or due to some other mechanism. In some embodiments, the subject has previously undergone treatment, and in some cases, the previous therapy has failed. In some embodiments, the subject is in remission. In some embodiments, the subject is post-menopausal. In some embodiments, the subject is at risk for breast cancer. Subjects are mammalian, and preferably are human, and more preferably are human females. In one embodiment, treatment is for patients that are non-responsive to tamoxifen, wherein non-responsiveness may be determined by a method selected from the group consisting of liver enzyme assay, genotyping Cyp2D6 for one or more copies of a partly or completely defective allele, for example the *10 allele, detecting the presence, absence, or levels of endoxifen in biological fluids, determining if the patient is taking drugs that interfere with tamoxifen metabolism, and combinations thereof.

In some embodiments, the breast cancer to be treated is ER positive. In some embodiments, the breast cancer is tamoxifen resistant or overexpresses Her2/Neu. In some embodiments, the breast cancer is recurring. In some embodiments, the breast cancer progression rate from ductal carcinoma in situ (DCIS) or atypical hyperplasia is reduced or delayed. The compounds may be used for the treatment of breast cancer, or for a reduction in the recurrence rate or severity of previously-treated breast cancer.

In one embodiment, the compound is administered as mono-therapy, where the compound according to the invention is the only agent active against breast cancer. In one embodiment, the monotherapeutically effective amount of compound according to the invention is bioequivalent to oral tamoxifen of 5-80 mg per day.

In one embodiment, the invention encompasses methods of treating breast cancer using a combination of two or more drugs. In combinations, each drug may be active individually against the breast cancer, or one or more drugs may be active against the breast cancer, and one or more additional drugs may serve to improve the efficacy of the active drug(s) by reducing side effects, increasing potency of the active drug(s), or some other mechanism. With regard to combination therapy, the two or more compounds (e.g., two, three, four, five, or more compounds) may be administered in combination, e.g., in the same formulation, or may be administered in separate formulations at the same or at different times. Pharmaceutical formulations of all combinations listed herein are also contemplated.

In one embodiment, compounds according to the invention are used in combination therapy with HDAC inhibitors such as valproic acid, trichostatin A, or SAHA; and/or IGF receptor inhibitors such as EGCG; and/or mTOR inhibitors such as rapamycin and/or sulforaphane; an EGFR inhibitor; and/or tamoxifen and related compounds; other chemotherapeutic agent, biologic, radiation therapy, or other agents and procedures useful in the treatment of cancer; and combinations thereof. In one embodiment, formula I, a HDAC inhibitor, and an IGF receptor inhibitor are administered. In another embodiment, the IGF receptor inhibitor is EGCG. In another embodiment, sulforaphane is also administered. In another embodiment, the breast cancer is ER positive.

In certain of the embodiments, the IGF-1R inhibitor can be picropodophyllin (see, e.g., Girnita, A. et al., Cancer Res., 2004. 64(1): 236-242) or the green tea polyphenol, EGCG (see, e.g., Shimizu, M. et al, Biochem. Biophys. Res. Commun., 2005. 334(3): 947-953; Li, M. et al., Cancer Epidemiol. Biomarkers Prev., 2007. 16(3): 598-605. An EGFR inhibitor may be gefitinib, and the mTOR inhibitor may be rapamycin or rapamycin derivatives (see, e.g., Johnston, S. R., Clin. Cancer Res., 2006. 12(3 Pt. 2): 1061-1069s). The skilled practitioner will be able to use a variety of IGF-1R, EGFR, and mTOR inhibitors in the invention, to provide therapeutically effective combinations.

Embodiments of the above combinations include administering formula I, EGCG, and sulforaphane; formula I, rapamycin, and sulforaphane; and formula I, EGCG, rapamycin, and sulforaphane. Sulforaphane may be administered at 01.-10 micromolar, 0.5-5 micromolar, 0.5-2 micromolar, or about 1 micromolar amounts. Additional embodiments include administering formula I and valproic acid; formula I, valproic acid, and EGCG; formula I, valproic acid, and rapamycin; and formula I, valproic acid, EGCG, and rapamycin. Embodiments of the above combinations include administering formula I and trichostatin A; formula I, trichostatin A, and EGCG; formula I, trichostatin A, and rapamycin; and formula I, trichostatin A, EGCG, and rapamycin. Embodiments of the above combinations include administering formula I and EGCG; formula I and rapamycin; and formula I, EGCG, and rapamycin.

When combinations are administered, dosages may be adjusted accordingly. In one embodiment, the daily dose of valproic acid is from about 15 mg/kg to about 60 mg/kg. In one embodiment, the daily dose of valproic acid is sufficient to achieve about 300 to about 867 micromolar in patient serum. In another embodiment, the daily dose of valproic acid is sufficient to achieve about 300 to about 1000 micromolar in patient serum, and in another embodiment, the daily dose of valproic acid is sufficient to achieve about 500 to about 1000 micromolar in patient serum. In some embodiments, the dose of SAHA is from about 200 mg/day to about 600 mg/day. In another embodiment, the dose of SAHA is about 400 mg/day. In one embodiment, the dose of EGCG is from about 300 mg/day to about 800 mg/day. In one embodiment, the dose of rapamycin is from about 0.125 mg/day to about 1 mg/day. In one embodiment, the dose of gefitinib is from about 200 mg/day to about 300 mg/day. In another embodiment, the dose of gefitinib is about 250 mg/day. In one embodiment, the dose of erlotinib is from about 100 mg/day to about 150 mg/day. In some embodiments, compounds are administered in combination, with ratios of those compounds which preserve the recommended daily doses of the compounds. In some embodiments, compounds are administered in combination, with ratios of those compounds which preserve the ranges of doses as described herein.

In another aspect, the invention provides a method of treating, reducing the recurrence rate, or reducing the severity of recurrence of breast cancer, the method comprising the step of administering a therapeutically effective amount of a compound according to the invention and a compound selected from the group consisting of a HDAC inhibitor or an IGF receptor inhibitor. In another aspect, the invention provides a method of treating, reducing the recurrence rate, or reducing the severity of recurrence of breast cancer, the method comprising the step of administering a therapeutically effective amount of a compound according to the invention and valproic acid. In another aspect, the invention provides a method of treating, reducing the recurrence rate, or reducing the severity of recurrence of breast cancer, the method comprising the step of administering a therapeutically effective amount of a compound according to the invention and sulforaphane.

In another aspect, the invention provides a method of treating, reducing the recurrence rate, or reducing the severity of recurrence of breast cancer, without attendant increase in risk of uterine cancer, the method comprising the step of administering a therapeutically effective amount of compound according to the invention with an HDAC inhibitor. In one embodiment, the HDAC inhibitor is VPA, TSA, sulforaphane, or SAHA. In another aspect, the invention provides a method of treating, reducing the recurrence rate, or reducing the severity of recurrence of breast cancer, without attendant increase in risk of uterine cancer, the method comprising the step of administering a therapeutically effective amount of compound according to the invention with an HDAC inhibitor, wherein the compound according to the invention has an estrogen-like effect on the uterus. Attendant risk of uterine cancer refers to reducing or eliminating the risk of uterine cancer that typically exists with anti-estrogen therapy alone. In some embodiments, this risk is reduced by 10%, 20%, 30%, 40%, 50%, 60%, 70%, 80%, 90%, 95%, or it is virtually or wholly eliminated. Prevention of breast cancer is also envisioned.

In one embodiment, the compound according to the invention is administered as part of a hormonal therapy. For example, hormonal therapy may be an antiestrogen therapy or aromatase inhibitor therapy. The hormonal therapy can also be estrogen ablation therapy, including an aromatase inhibitor. According to the invention, the aromatase inhibitor can be, but is not limited to, exemestane, letrozole, or anastrozole. In one embodiment, the dose of letrozole is from about 1 mg/day to about 5 mg/day. In another embodiment, the dose of letrozole is about 2.5 mg/day. In one embodiment, the dose of exemestane is from about 10 mg/day to about 40 mg/day. In another embodiment, the dose of exemestane is about 25 mg/day. In yet another embodiment, the dose of anastrozole is from about 0.5 mg/day to about 3 mg/day. In another embodiment, the dose of anastrozole is about 1 mg/day.

In one embodiment, the compound according to the invention is administered in combination with 4-hydroxytamoxifen or a prodrug of 4-hydroxytamoxifen. In one embodiment, the ratio of compound according to the invention to 4-hydroxytamoxifen or prodrug thereof is the bioequivalent of from about 0.5 to about 10 times endoxifen to 4-hydroxytamoxifen. In one embodiment, levels of endoxifen are about 4 times the level of 4-hydroxytamoxifen up to endoxifen levels of about 6 times the level of 4-hydroxytamoxifen. Bioequivalence may be determined by assay of serum levels, or by levels in plural effusion, among other methods of determining bioequivalence. Prevention of breasts cancer is also envisioned.

In some embodiments, the present invention encompasses methods and compositions for reducing the incidence of breast cancer or delaying the progression of pre-cancerous conditions, including in subjects who are at risk for breast cancer that is greater than the average risk for breast cancer. Risk factors considered in preventing breast cancer in subjects include family history of breast cancer (relatives with breast cancer), genetic markers for breast cancer such as BRCA1 and BRCA2, age at menarche, age at first live birth, the number of breast biopsies, presence of atypical hyperplasia on breast biopsy, population rates of breast cancer and death from other causes. The present invention also provides methods and compositions for reducing the rate of progression of breast cancer to a later stage for those who already have breast cancer or precancerous indicators, as well as reducing the rate and/or severity of the recurrence of breast cancer for those in remission from breast cancer.

In some embodiments, the invention contemplates methods of delaying the progression of DCIS to breast cancer, and methods of delaying the progression of atypical hyperplasia to breast cancer. In some preferred embodiments, the invention encompasses treating estrogen receptor positive breast cancer. In yet another embodiment, the present invention encompasses treating DCIS and, in another embodiment, the present invention encompasses treating atypical hyperplasia.

The present invention further contemplates that the combination therapies as described herein can also reduce or eliminate other side effects of treatment, at least in part because lower doses of compounds can be used in treatment or prevention protocols.

It is within the scope of the invention to treat breast cancer that is tamoxifen resistant, as well as to treat breast cancer that overexpresses Her2/Neu. The invention also contemplates treating subjects with breast cancer for whom previous therapy has failed, or for whom the cancer is recurring. In some embodiments of the invention, the invention is to treat subjects with breast cancer who are post-menopausal, and in some embodiments, the invention contemplates treating subjects who are genetically predisposed to breast cancer or otherwise at increased risk. The invention also encompasses methods of treating subjects to prevent progression of breast cancer, and in some embodiments, the invention encompasses treating or preventing breast cancer in patients with pre-cancerous growths or benign tumors. It is within the scope of the invention to treat subjects that are in remission from breast cancer, and to treat subjects with breast cancer that have previously undergone treatment.

In one embodiment, intermediates are presented for the synthesis of compounds and compositions for the treatment and prevention of breast cancer. The intermediates may be immediate precursors of the compounds to be administered to the patient, or the intermediates may require two or more synthetic steps to be converted into a compound to be administered to a patient.

4. BRIEF DESCRIPTION OF THE FIGURES

5. DETAILED DESCRIPTION OF THE INVENTION

Figure 1:
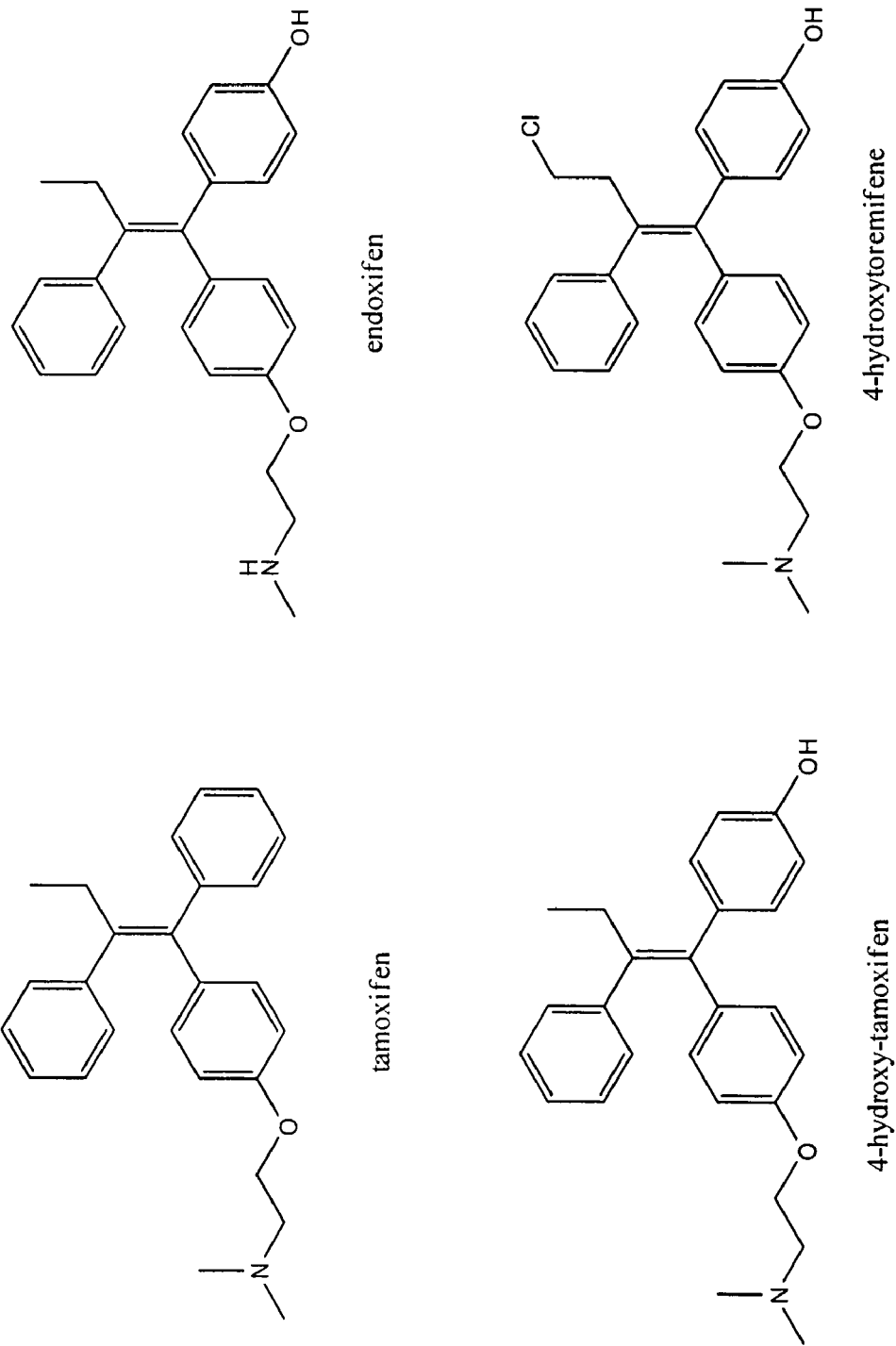
FIG. 1 shows the chemical structures for tamoxifen, 4-hydroxy-tamoxifen, endoxifen, and 4-hydroxytoremifene.

While not wishing to be bound by theory, it is believed that the compounds, compositions, and methods of the instant invention overcome the deficiencies of the prior art with regard to treatment of breast cancer. Again, while not wishing to be bound by theory, it is believed that in some cases of breast cancer, non-responsiveness may be due to lack of the proper enzymatic machinery for the in vivo conversion of tamoxifen into endoxifen, and/or the poor bioavailability of endoxifen resulting from possible glucuronidation, or from lack of sufficient binding between the active agent and a receptor. Alternatively, endoxifen may have highly variable bioavailability among patient groups or subpopulations. The present inventors find that these and other problems can be overcome by appropriate chemical modification and/or de novo synthesis of compounds of Formula I or II. In a preferred example, a phosphate group is attached at the 4-hydroxy position of compounds according to the invention. While not wishing to be bound by theory, it is believed that this modification and other modifications can lead to improved clinical outcomes for breast cancer patients.

5.1 Definitions

As used herein, the term "prodrug" means a compound with a temporary modification of a functional group of a drug in order to improve the pharmaceutical utility of the drug. Prodrug may refer to the entire compound, or it may refer to the chemical modification, in the context of a prodrug moiety being the chemical modification. In some embodiments, the functional group of the drug is a handle for the introduction of a moiety that confers on the new entity some desirable characteristic. In other embodiments, the prodrug moiety is intimately connected with the pharmaceutical deficiency of the parent drug, and the presence of the prodrug moiety directly addresses the deficiency. In some embodiments, prodrugs rely on in vivo enzymatic activation for conversion to active form of the drug for example by cleavage of the prodrug moiety by an enzyme. In other embodiments, prodrugs rely on physiological chemical conditions for release of the drug, for example through a change in pH. The benefits of a prodrug are not limited to improved in vivo benefits compared to the parent drug, but may also include improved processing or storage characteristics or economic considerations prior to administration to the patient.

As used herein, the term "cancer" refers to a disease involving cells that have the potential to metastasize to distal sites and exhibit phenotypic traits that differ from those of non-cancer cells. Cancer cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless replicative potential, and sustained angiogenesis. The term "cancer cell" is meant to encompass both pre-malignant and malignant cancer cells.

"Estrogen receptor positive breast cancer" refers to breast cancers that are in the positive or intermediate range for the estrogen receptor protein. For example, when estrogen receptor protein can be measured as femtomoles per milligram of cytosol protein. In this assay, values above 10 are positive, values from 3 to 10 are intermediate, and values less than 3 are negative. Other assays known in the art can be used to determined if the breast cancer is estrogen receptor positive, in particular assays based on antibodies to estrogen receptors alpha and beta and their use in biochemical or histological assays.

The terms "histone deacetylase inhibitor" and "inhibitor of histone deacetylase" mean a compound which is capable of interacting with a histone deacetylase and inhibiting its enzymatic activity, abbreviated as HDAC inhibitors. "Inhibiting histone deacetylase enzymatic activity" means reducing the ability of a histone deacetylase to remove an acetyl group from a histone. (see, e.g., Minucci et al., Nature 6:38-51 (2006). In some preferred embodiments, such reduction of histone deacetylase activity is at least about 50%, more preferably at least about 75%, and still more preferably at least about 90%. In other preferred embodiments, histone deacetylase activity is reduced by at least 95% and more preferably by at least 99%. Assays for determining inhibition are described in Phiel, C. J., et al., J Biol. Chem., 2001. 276(39): p. 36734-41 and Gottlicher, M., et al., Embo J., 2001. 20(24): p. 6969-78.

Preferably, such inhibition is specific, i.e., the histone deacetylase inhibitor reduces the ability of a histone deacetylase to remove an acetyl group from a histone at a concentration that is lower than the concentration of the inhibitor that is required to produce another, unrelated biological effect. Preferably, the concentration of the inhibitor required for histone deacetylase inhibitory activity is at least 2-fold lower, more preferably at least 5-fold lower, even more preferably at least 10-fold lower, and most preferably at least 20-fold lower than the concentration required to produce an unrelated biological effect.

As used herein, the term "active ingredient" includes having a therapeutic or prophylactic effect on breast cancer in the combinations. This does not include inactive ingredients such as pharmaceutical carriers, excipients, and the like.

"Mammalian target of rapamycin protein inhibitor" or "mTOR inhibitor" includes drugs such as rapamycin, temsirolimus, and everolimus that selectively inhibit the mammalian target of rapamycin (mTOR).

"IGF-1 receptor inhibitor" refers to drugs such as picrophodophyllin and podophyllotoxin that selectively inhibit the IGF-1 receptor.

"EGF receptor inhibitor" of "EGFR inhibitor" refers to drugs such as gefitinib and erlotinib that selectively inhibit the EGF receptor.

"Insufficient to fully prevent production of estrogen" refers to the inability of an aromatase inhibitor to fully prevent a tumor cell from converting an estrogen precursor into a functional estrogen that can stimulate tumor proliferation.

"Less than estrogen receptor-saturating amounts" refers to amounts of fulvestrant less than 100 fold molar excess to the amounts of estradiol or less than 10 nanomolar in patient circulation.

"Hormonal therapy" refers to drugs or treatments that block the effect of, or reduce the levels of hormones, and in particular which block the effect of estrogen or lower estrogen levels, including anti-estrogen therapy and estrogen ablation therapy.

As used herein, the terms "prevent," "preventing" and "prevention" refer to the prevention of the recurrence, worsening, or spread of a disease in a subject resulting from the administration of a prophylactic or therapeutic agent.

The terms "overexpress," "overexpression" or "overexpressed" interchangeably refer to a protein or nucleic acid (RNA) that is translated or transcribed at a detectably greater level, usually in a cancer cell, in comparison to a normal cell. The term includes overexpression due to transcription, post transcriptional processing, translation, post-translational processing, cellular localization (e.g., organelle, cytoplasm, nucleus, cell surface), and RNA and protein stability, as compared to a normal cell. Overexpression can be detected using conventional techniques for detecting mRNA (i.e., RT-PCR, PCR, hybridization, microarray) or proteins (i.e., ELISA, immunohistochemical techniques). Overexpression can be 10%, 20%, 30%, 40%, 50%, 60%, 70%, 80%, 90% or more in comparison to a normal cell. In certain instances, overexpression is 1-fold, 2-fold, 3-fold, 4-fold or more higher levels of transcription or translation in comparison to a normal cell.

As used herein, the term "in combination" refers to the use of more than one prophylactic and/or therapeutic agents. The use of the term "in combination" does not restrict the order in which prophylactic and/or therapeutic agents are administered to a subject with cancer, especially breast cancer. A first prophylactic or therapeutic agent can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, hours, 96 hours, 1 week, 2 weeks, 3 weeks, 4 weeks, 5 weeks, 6 weeks, 8 weeks, or 12 weeks after) the administration of a second prophylactic or therapeutic agent to a subject which had, has, or is susceptible to cancer, especially breast cancer. The prophylactic or therapeutic agents are administered to a subject in a sequence and within a time interval such that the agent of the invention can act together with the other agent to provide an increased benefit than if they were administered otherwise. Any additional prophylactic or therapeutic agent can be administered in any order with the other additional prophylactic or therapeutic agents.

As used herein, the term "combine effectively" refers to a combination of therapies (e.g., a combination of prophylactic or therapeutic agents) which is more effective than any single agent administered alone. Combining effectively may also refer to combinations of therapies that are not less effective than any single agent or even less effective than any single agent, but which also eliminate or reduce the adverse effects of one or more of the agents, such as eliminating or reducing the risk of uterine cancer associated with one or more of the agents.

As used herein, the term "synergistic" refers to a combination of therapies (e.g., a combination of prophylactic or therapeutic agents) which is more effective than the additive effects of any two or more single agents. A synergistic effect of a combination of therapies permits the use of lower dosages of one or more of the therapies and/or less frequent administration of said therapies (e.g., agents) to a subject with a disease or disorder, in particular, cancer, or a condition or symptom associated therewith. The ability to utilize lower dosages of therapies and/or to administer said therapies less frequently reduces the toxicity associated with the administration of said therapies to a subject without reducing the efficacy of said therapies in the prevention, management, or treatment of a disease or disorder, in particular, cancer or a condition or symptom associated therewith. In addition, a synergistic effect can result in improved efficacy of therapies in the prevention, management, or treatment of a disease or disorder, in particular, cancer or a condition or symptom associated therewith. Finally, the synergistic effect of a combination of therapies may avoid or reduce adverse or unwanted side effects associated with the use of any single therapy.

As used herein, the phrase "side effects" encompasses unwanted and adverse effects of a prophylactic or therapeutic agent. Adverse effects are always unwanted, but unwanted effects are not necessarily adverse. An adverse effect from a prophylactic or therapeutic agent might be harmful or uncomfortable or risky. Side effects can refer specifically to an increase in uterine cell proliferation, as well as to an increase in the frequency of uterine cancer and an increase in the risk of developing uterine cancer. Side effects from chemotherapy include, but are not limited to, gastrointestinal toxicity such as, but not limited to, early and late-forming diarrhea and flatulence, nausea, vomiting, anorexia, leucopenia, anemia, neutropenia, asthenia, abdominal cramping, fever, pain, loss of body weight, dehydration, alopecia, dyspnea, insomnia, dizziness, mucositis, xerostomia, and kidney failure, as well as constipation, nerve and muscle effects, temporary or permanent damage to kidneys and bladder, flu-like symptoms, fluid retention, and temporary or permanent infertility. Side effects from radiation therapy include but are not limited to fatigue, dry mouth, and loss of appetite. Side effects from biological therapies/immunotherapies include but are not limited to rashes or swellings at the site of administration, flu-like symptoms such as fever, chills and fatigue, digestive tract problems and allergic reactions. Side effects from hormonal therapies include but are not limited to nausea, fertility problems, depression, loss of appetite, eye problems, headache, and weight fluctuation. Additional undesired effects typically experienced by patients are numerous and known in the art. Many are described in the Physicians' Desk Reference (56$^{th}$ ed., 2002).

"Without attendant risk in increase of uterine cancer" refers to a lowered or eliminated risk of developing uterine cancer as compared to patients who have an increased risk for developing uterine cancer due to a course of anti-estrogen therapy.

By "therapeutically effective amount or dose" or "therapeutically sufficient amount or dose" or "effective or sufficient amount or dose" herein is meant a dose that produces therapeutic effects for which it is administered, in the context of the combination therapy in which it is administered. Often, the therapeutically effective or sufficient amount or dose of the compounds comprising the pharmaceutical compositions of the invention will be lower when administered in the specific combinations, than the doses that would be therapeutically effective or sufficient when the compounds are administered separately. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and Remington. *The Science and Practice of Pharmacy*, 20th Edition, 2003, Gennaro, Ed., Lippincott, Williams & Wilkins). In some embodiments, a therapeutically effective amount refers to that amount of the therapeutic agent sufficient to destroy, modify, control or remove primary, regional or metastatic cancer tissue. A therapeutically effective amount may refer to the amount of therapeutic agent sufficient to delay or minimize the spread of cancer. A therapeutically effective amount may also refer to the amount of the therapeutic agent that provides a therapeutic benefit in the treatment or management of cancer. Further, a therapeutically effective amount with respect to a therapeutic agent of the invention means that amount of therapeutic agent alone, or in combination with other therapies, that provides a therapeutic benefit in the treatment or management of cancer. In sensitized cells, the therapeutically effective dose can often be lower than the conventional therapeutically effective dose for non-sensitized cells. In some embodiments, a therapeutically effective amount refers to the amount of a therapeutic agent that, e.g., reduces the proliferation of cancer cells, increases the death of cancer cells or, reduces the size of a tumor or spread of a tumor in a subject. Preferably, a therapeutically effective amount of a therapeutic agent reduces the size of a tumor or the spread of a tumor in a subject by at least 5%, preferably at least 10%, at least 15%, at least 20%, at least 25%, at least 30%, at least 35%, at least 40%, at least 45%, at least 50%, ate least 55%, at least 60%, at least 65%, at least 70%, at least 75%, at least 80%, at least 85%, at least 90%, at least 95% or at least 99% relative to a control such as PBS. In some embodiments, a therapeutically effective amount refers to the amount of a therapeutic agent that increases survival by 1 month, 2 months, 6 months, 1 year, 2 years, 3 years, 4 years, 5 years, 6 years, 7 years, 8 years, 9 years, 10 years, or more. In some embodiments, a therapeutically effective amount refers to the amount of a therapeutic agent that prevents the progression from DCIS or atypical hyperplasia to breast cancer.

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E.W. Martin. Such compositions will contain a prophylactically or therapeutically effective amount of a prophylactic or therapeutic agent preferably in purified form, together with a suitable amount of carrier so as to provide the form for proper administration to the patient. The formulation should suit the mode of administration. In a preferred embodiment, the pharmaceutical compositions are sterile and in suitable form for administration to a subject, preferably an animal subject, more preferably a mammalian subject, and most preferably a human subject.

The term "linker" means a divalent chemical moiety that, when present (i.e., when n is >0), connects the nitrogen atom of Formula I or II with $R_3$ through one or more atoms interspersed with covalent bonds. Examples of linkers are known in the art, such as polyamines, polyethylene glycol, polypropylene glycol, polypeptides, carbohydrates, and the like. A linker may alternately be referred to as a spacer.

The term "polyfluoroalkyl" means an alkyl group with one or more fluorines. In a preferred embodiment, "polyfluoroalkyl" means two or more fluorines, up to and including perfluoroalkyl groups.

As used herein, the term "intermediates" encompasses compounds used in the synthesis of prodrug compounds according to the invention. Such intermediates may have activity in their own right, or may be biologically inactive.

5.2 Pharmaceutical Formulations

Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences*, 20$^{th}$ ed., 2003).

It may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering one or more prophylactic or therapeutic agents, care must be taken to use materials to which the prophylactic or therapeutic agents do not absorb.

The invention can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, pp. 317-327; see generally above).

The composition can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the antibodies of the invention or fragments thereof (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; International Publication No. WO 99/15154; and International Publication No. WO 99/20253. Examples of polymers used in sustained release formulations include, but are not limited to, poly(2-hydroxy ethyl methacrylate), poly(methyl methacrylate), poly(acrylic acid), poly (ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the therapeutic target, i.e., the lungs, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more antibodies of the invention or fragments thereof. See, e.g., U.S. Pat. No. 4,526,938, International publication No. WO 91/05548, International publication No. WO 96/20698, Ning et al., 1996, "Intratumoral Radioimmunotheraphy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entirety.

A pharmaceutical composition of the invention is formulated to be compatible with its intended route of administration. Examples of suitable routes of administration include, but are not limited to, ingestion, parenteral (e.g., intravenous, intramuscular, intradermal, intra-tumoral, intra-synovial, and subcutaneous), oral (e.g., inhalation, ingestion), intranasal, transdermal (topical), transmucosal, intra-tumoral, intra-synovial, vaginal, and rectal administration. In a specific embodiment, the composition is formulated in accordance with routine procedures as a pharmaceutical composition adapted for intravenous, subcutaneous, intramuscular, oral, e.g. ingestion, intra-tumoral, intra synovial, intranasal or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If the compositions of the invention are to be administered topically, the compositions can be formulated in the form of, e.g., a toothpaste, ointment, cream, transdermal patch, lotion, gel, oral gel, shampoo, spray, aerosol, solution, emulsion, or other form well-known to one of skill in the art. See, e.g., Remington's Pharmaceutical Sciences and Introduction to Pharmaceutical Dosage Forms, 4th ed., Lea & Febiger, Philadelphia, Pa. (1985). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as Freon), or in a squeeze bottle. Moisturizers or humectants can also be added to pharmaceutical compositions and dosage forms if desired. Examples of such additional ingredients are well-known in the art.

If the compositions of the invention are to be administered intranasally, the compositions can be formulated in an aerosol form, spray, mist or in the form of drops. In particular, prophylactic or therapeutic agents for use according to the present invention can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

If the compositions of the invention are to be administered orally, the compositions can be formulated orally in the form of, e.g., gum, tablets, capsules, cachets, gelcaps, solutions, suspensions and the like. Tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated for slow release, controlled release or sustained release of a prophylactic or therapeutic agent(s).

The compositions of the invention may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compositions of the invention may also be formulated in rectal compositions such as suppositories or retention enemas, e.g., containing conventional suppository bases such as cocoa butter or other glycerides.

In addition to the formulations described previously, the compositions of the invention may also be formulated as a depot preparation. Such long acting formulations may be administered by implantation (for example subcutaneously or intramuscularly) or by intramuscular injection. Thus, for example, the compositions may be formulated with suitable polymeric or hydrophobic materials (for example as an emulsion in an acceptable oil) or ion exchange resins, or as sparingly soluble derivatives, for example, as a sparingly soluble salt.

Generally, the ingredients of compositions of the invention are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

5.3 Kits

The invention provides a pharmaceutical pack or kit comprising one or more containers filled with individual components (in pharmaceutical formulations) of the combination therapies described herein; for example, contained filled with an HDAC inhibitor and one or more hormonal therapy agents, and/or one or more therapeutic or prophylactic agents such as an IGF-1R inhibitor, an EGFR inhibitor, an mTOR inhibitor, or another active ingredient. Containers may also be filled with an HDAC inhibitor, and one or more therapeutic or prophylactic agents such as an IGF-1R inhibitor, an EGFR inhibitor, an mTOR inhibitor, and/or another active ingredient. The pharmaceutical pack or kit may further comprises one or more other prophylactic or therapeutic agents useful for the treatment of a disease or disorder. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides pharmaceutical packs or kits that can be used in the above methods. The kit may further comprises one or more other prophylactic or therapeutic agents, or active ingredients useful for the treatment of cancer in one or more containers. In other embodiments, the kit may comprise at least one compound according to the invention, at least one HDAC inhibitor, and one or more of at least one or more of an IGF-1R inhibitor, an EGFR inhibitor or mTOR inhibitor. Examples of such agents and compounds are disclosed above.

5.4 Articles of Manufacture

The present invention also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient is sterile and suitable for administration as a particulate free solution. In other words, the invention encompasses both parenteral solutions and lyophilized powders, each being sterile, and the latter being suitable for reconstitution prior to injection. Alternatively, the unit dosage form may be a solid suitable for oral, transdermal, intratumoral, intra-synovial, topical or mucosal delivery.

In a specific embodiment, the unit dosage form is suitable for intravenous, intramuscular, intratumoral, intra-synovial, or subcutaneous delivery. Thus, the invention encompasses solutions, preferably sterile, suitable for each delivery route.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures (such as methods for monitoring mean absolute lymphocyte counts, tumor cell counts, calcium concentration, and tumor size) and other monitoring information.

More specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material.

In a specific embodiment, an article of manufacture comprises packaging material and a pharmaceutical agent and instructions contained within said packaging material, and a pharmaceutically acceptable carrier, and said instructions indicate a dosing regimen for preventing, treating or managing a subject with cancer. In another embodiment, an article of manufacture comprises packaging material and a pharmaceutical agent and instructions contained within said packaging material, and said instructions indicate a dosing regimen for preventing, treating or managing a subject with a cancer.

In therapeutic use for the treatment of cancer, the compounds utilized in the pharmaceutical method of the invention are administered at the initial dosage of about 0.001 mg/kg to about 100 mg/kg daily. A daily dose range of about 0.01 mg/kg to about 50 mg/kg, or about 0.1 mg/kg to about 20 mg/kg, or about 1 mg/kg to about 10 mg/kg, or about 1 mg/kg to about 5 mg/kg, can be used. The dosages, however, may be varied depending upon the requirements of the patient, the severity of the condition being treated, and the compound being employed. For example, dosages can be empirically determined considering the type and stage of cancer diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician.

5.5 Characterization and Demonstration of Therapeutic or Prophylactic Utility Toxicity and efficacy of the prophylactic and/or therapeutic treatments and protocols of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

In order to determine therapeutic or prophylactic utility, it is encompassed by the present invention to use any of the assays described herein, as well as those known in the art. Also encompassed by the invention to determine therapeutic or prophylactic utility are any relevant cancer, and more specifically, breast cancer animal models. For example, one may utilize a an MCF-7 xenograft model, or a modified MCF-7 xenograft model (Hale L. V. et al., 1997, Lab Anim Sci., 47(1):82-85). Further encompassed by the invention, pending safety and efficacy, are clinical trials to assess the compounds and methods of the present invention.

5.6 Embodiments

Compounds

The present invention is directed to compounds, compositions thereof, and the use of the compounds and compositions for the treatment and prevention of breast cancer. Compounds according to the invention may be considered prodrugs and related compounds. The compounds may be used for the treatment of breast cancer, or for a reduction in the recurrence rate or severity of previously-treated breast cancer.

According to one embodiment, the invention is a compound of formula I or formula II:

and pharmaceutically acceptable salts thereof, wherein X is H, O, or S; $R_1$ is H or a prodrug moiety, or not present when X is H; $R_2$ is H, $CH_3$, a lower alkyl group, a divalent cyclic alkyl group forming a quaternary ammonium, or a prodrug moiety; $R_3$ is a polyfluoro alkyl group; n is an integer from 0 to 10; and Y is a linker. While the compounds of Formula I and II are drawn with a specific orientation around the double bond, both E and Z configurations around the double bond are encompassed by the invention, individually as compounds and together in equimolar or non-equimolar mixtures in compositions.

According to another embodiment, the invention is a compound as described above, wherein $R_3$ is selected from a $C_1$-$C_6$ polyfluoroalkyl group. In one embodiment, $R_3$ is selected from a $C_1$-$C_6$ perfluoroalkyl group. Alternately, the compound contains $R_3$, which is selected from perfluoromethyl and perfluoroethyl.

In one embodiment, Y is —$R_4SR_5$—, —$R_4SOR_5$—, —$R_4SO_2R_5$—, —$R_4OR_5$—, —$R_4NR_2R_5$—, —$R_4NR_2COR_5$—, —$R_4CONR_2R_5$—, —$R_4COR_5$—, —$R_4C(=O)OR_5$—, —$R_4OC(=O)R_5$—, —$R_4POR_5$—, —$R_4OP(=O)(OH)OR_5$—, —$R_4NR_2C(=NR_2)NR_2R_5$—, —$R_4NR_2C(=O)NR_2R_5$—, —$R_4NR_2C(=O)OR_5$—, and —$R_4OC(=O)NR_2R_5$—; wherein $R_2$ is as defined above, and $R_4$ and $R_5$ are independently selected from $C_1$-$C_{10}$ straight-chain, branched, or cyclic alkyl, $C_2$-$C_{10}$ straight-chain, branched, or cyclic alkenyl, $C_2$-$C_{10}$ straight-chain or branched alkynyl, divalent aryl, and divalent heterocyclyl groups. In a preferred embodiment, Y is —$R_4OR_5$— or —$R_4NR_2R_5$—. Preferably, n is an integer from 2 to 4.

In one embodiment, the compounds according to the invention are compounds of the following formulas:

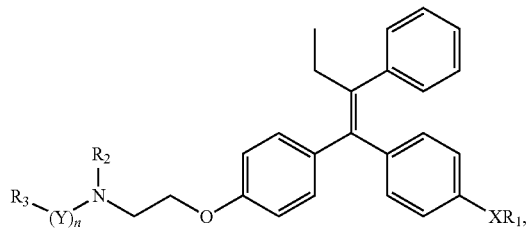

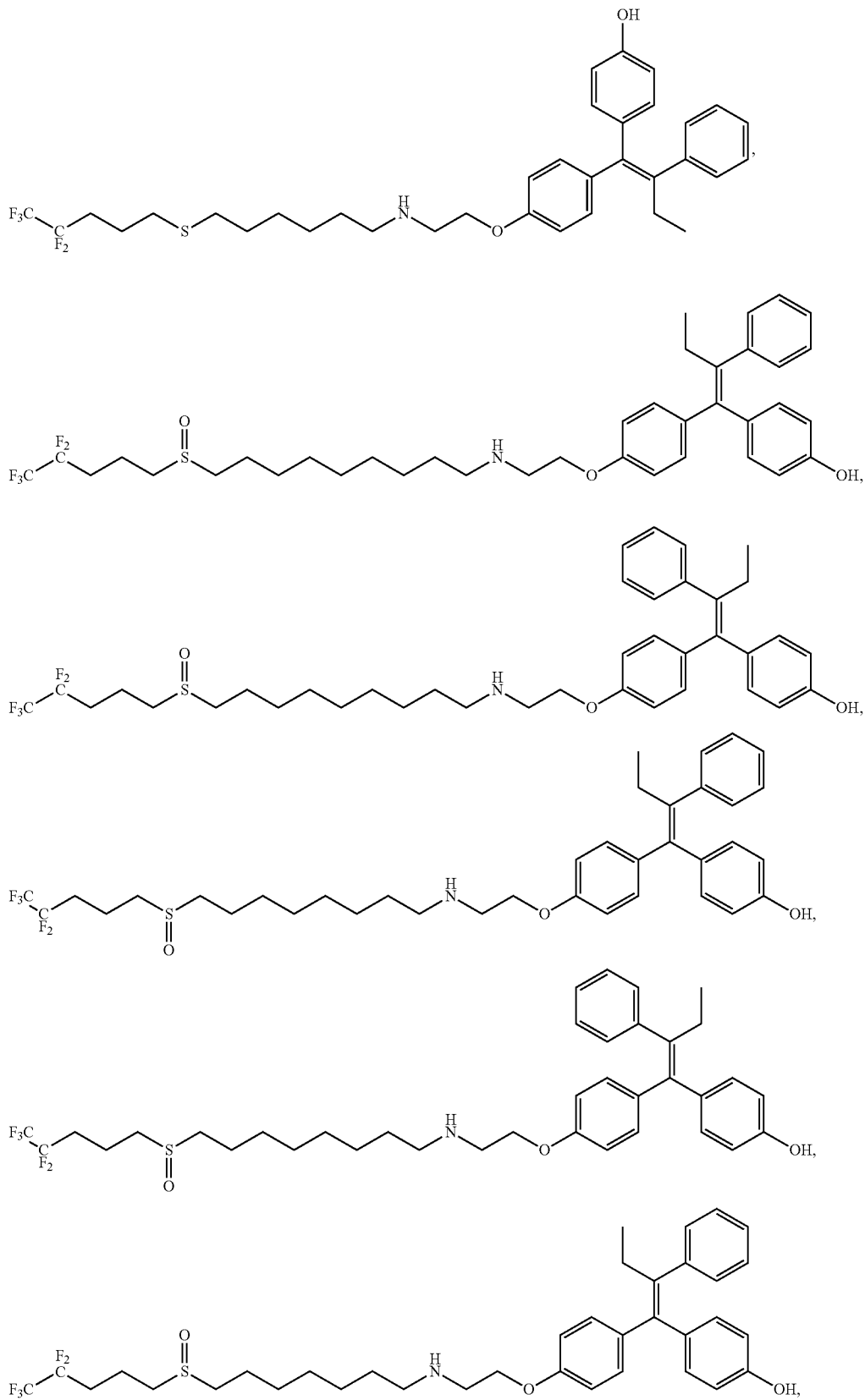

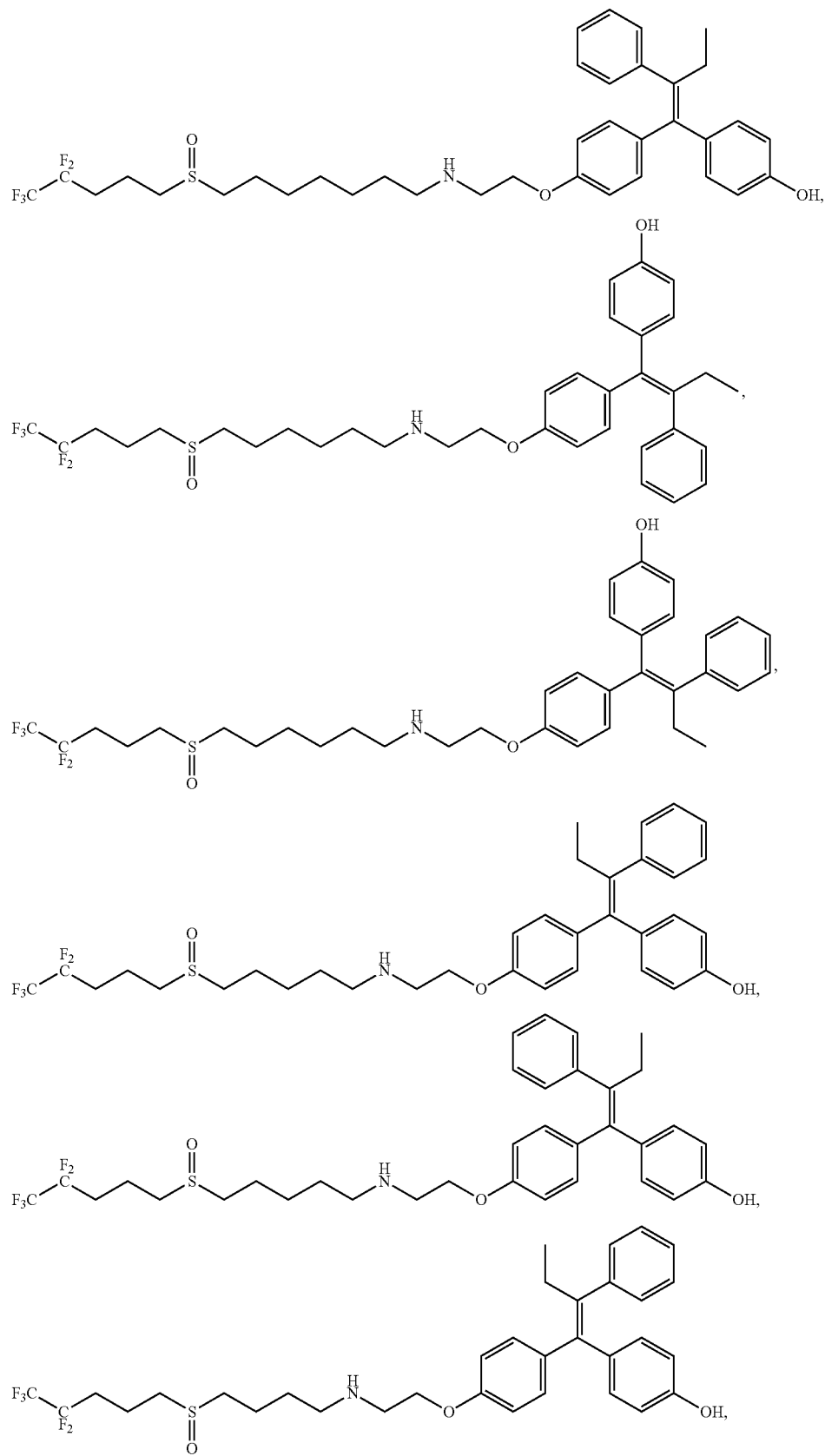

-continued

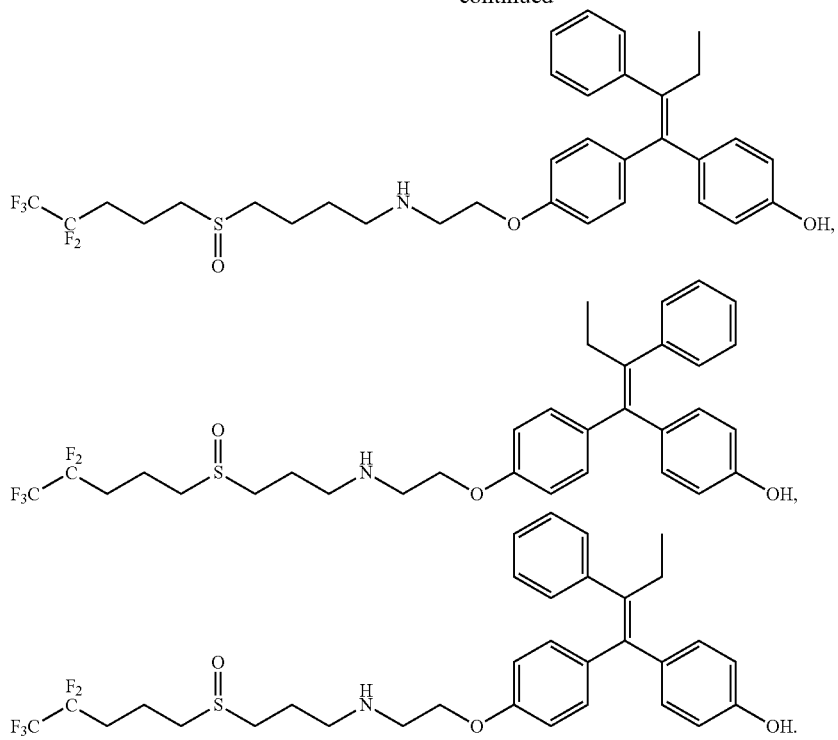

In various embodiments, $R_1$, $R_2$, $R_4$, and $R_5$ are each independently selected from the following groups:

Alkyl groups preferably having from 1 to 12 carbon atoms. A preferred class of alkyl groups has 1 to about 8 carbon atoms, still more preferably 1 to about 6 carbon atoms, and most preferably 1, 2, 3 or 4 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members. Lower alkyl groups refers may refer to alkyl groups with 1 to 6 carbon atoms.

Alkenyl and alkynyl groups having one or more unsaturated linkages and from 2 to about 12 carbon atoms, more preferably 2 to about 8 carbon atoms, still more preferably 2 to about 6 carbon atoms, even more preferably 2, 3 or 4 carbon atoms. The terms alkenyl and alkynyl as used herein refer to both cyclic and noncyclic groups, although straight or branched noncyclic groups are generally more preferred.

Alkylidene groups, branched or unbranched, and preferably having from 1 to 12 carbon atoms. One more preferred class of alkylidene groups has from 1 to about 8 carbon atoms, yet more preferably from 1 to about 6 carbon atoms, and most preferably 1, 2, 3 or 4 carbon atoms. Methylidene, ethylidene and propylidene including isopropylidene are particularly preferred alkylidene groups in the compounds of the present invention.

Alkylsulfinyl groups having one or more sulfoxide (SO) groups and from 1 to about 12 carbon atoms, more preferably from 1 to about 8 carbon atoms, and still more preferably 1 to about 6 carbon atoms. Alkylsulfinyl groups having 1, 2, 3 or 4 carbon atoms are particularly preferred.

Alkylsulfonyl groups having one or more sulfonyl ($SO_2$) groups and from 1 to about 12 carbon atoms, more preferably from 1 to about 8 carbon atoms, and still more preferably 1 to about 6 carbon atoms. Alkylsulfonyl groups having 1, 2, 3 or 4 carbon atoms are particularly preferred.

Aminoalkyl groups having one or more primary, secondary and/or tertiary amine groups, and from 1 to about 12 carbon atoms, more preferably 1 to about 8 carbon atoms, still more preferably 1 to about 6 carbon atoms, even more preferably 1, 2, 3 or 4 carbon atoms. Secondary and tertiary amine groups are generally more preferred than primary amine moieties.

Heterocyclic groups including heteroaromatic and heteroalicyclic groups. Suitable heteroaromatic groups in the compounds of the present invention contain one, two or three heteroatoms selected from N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl and benzothiazol. Suitable heteroalicyclic groups in the compounds of the present invention contain one, two or three heteroatoms selected from N, O or S atoms and include, e.g., tetrahydrofuranyl, tetrahydropyranyl, piperidinyl, morpholino and pyrrolidinyl groups.

Aryl groups including single and multiple ring compounds, including multiple ring compounds that contain separate and/or fused aryl groups. Typical aryl groups contain from 1 to 3 separated or fused rings and from 6 to about 18 carbon ring atoms. Specifically preferred aryl groups include substituted or unsubstituted phenyl, naphthyl, biphenyl, phenanthryl, and anthracyl.

References herein to substituted groups in the compounds of the present invention refer to the specified moiety, typically alkyl or alkenyl, that may be substituted at one or more available positions by one or more suitable groups, e.g., halogen such as fluoro, chloro, bromo and iodo; cyano; hydroxyl; nitro; azido; carboxamido; alkyl groups including those groups having 1 to about 12 carbon atoms, preferably from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having those having one or more oxygen linkages and from 1 to about 12 carbon atoms, preferably from 1 to about 6 carbon atoms; aryloxy such as phenoxy; alkylthio groups including those moieties having one or more thioether linkages and from 1 to about 12 carbon atoms, preferably from 1 to about 6 carbon atoms; alkylsulfinyl groups including those moieties having one or more sulfinyl linkages and from 1 to about 12 carbon atoms, preferably from 1 to about 6 carbon atoms; alkylsulfonyl groups including those moieties having one or more sulfonyl linkages and from 1 to about 12 carbon atoms, preferably from 1 to about 6 carbon atoms; aminoalkyl groups such as groups having one or more N atoms and from 1 to about 12 carbon atoms, preferably from 1 to about 6 carbon atoms; aryl having 6 or more carbons, particularly phenyl; aralkyl such as benzyl; heterocyclic groups including heteroalicyclic and heteroaromatic groups, especially with 5 to 10 ring atoms of which 1 to 4 are heteroatoms, more preferably heterocyclic groups with 5 or 6 ring atoms and 1 or 2 heteroatoms or with 10 ring atoms and 1 to 3 heteroatoms.

Preferred $R_1$, $R_2$, $R_4$, and $R_5$ groups include alkyl, alkenyl and alkynyl that may be substituted at one or more available positions by one or more suitable groups, e.g., halogen such as fluoro, chloro, bromo and iodo, especially ω-chloro or perfluoro; aminoalkyl groups such as groups having one or more N atoms and from 1 to about 12 carbon atoms, preferably from 1 to about 6 carbon atoms; aryl having 6 or more carbons, particularly phenyl; aralkyl such as benzyl; heterocyclic groups including heteroalicyclic and heteroaromatic groups, especially with 5 to 10 ring atoms of which 1 to 4 are heteroatoms, more preferably heterocyclic groups with 5 or 6 ring atoms and 1 or 2 heteroatoms or with 10 ring atoms and 1 to 3 heteroatoms, the heterocyclic groups optionally being substituted with one or more of the substituents, especially amino such as dimethylamino or with keto.

In various embodiments, $R_3$ is independently selected from $C_1$-$C_{12}$ perfluoroalkyl, perfluoroalkenyl, and perfluoroalkynyl groups. According to another embodiment, the invention is a compound as described above, wherein $R_3$ is selected from a $C_1$-$C_6$ perfluoroalkyl group. Alternately, the compound contains $R_3$, which is selected from perfluoromethyl and perfluoroethyl.

Various prodrugs are known in the art. For example, see Simplicio et al., "Prodrugs for Amines," Molecules, vol. 13, iss. 3, pp. 519-547, March 2008, available from the internet at <<http://www.mdpi.org>>; see also Larsen, C. S., et al., "Chapter 14: Design and application of prodrugs" from Textbook of Drug Design and Discovery, Third Edition, edited by Krogsgaard-Larsen, P. et al., pages 410-458, 2002. The contents of each publication are incorporated by reference.

In some embodiments, the prodrug moiety may be selected from Table 1, as adapted from Simplicio, in particular for a prodrug moiety to be attached to a nitrogen, where R groups in a figure may be the same or different:

TABLE 1

| Prodrug type | mechanism of transformation | advantages | disadvantages |
| --- | --- | --- | --- |
| 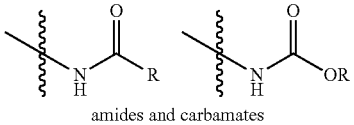<br>amides and carbamates | enzymatic, pH activated | lipid solubility may be improved slow release | Needs to be activated by an electron withdrawing substitute |
| 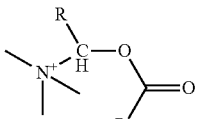<br>N-acyloxyalkylderivatives | enzymatic followed by spontaneous | improved lipophilicity | only applicable to tertiary amines |
| 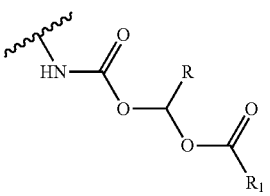<br>N-acyloxyalkoxy carbonyl derivatives | enzymatic followed by spontaneous | produces neutral compounds | usually not suitable for primary amines |
| 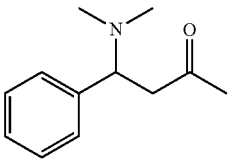<br>β-aminoketones | pH activated | lowers pKa increases lipophilicity | easily hydrolyzed in aqueous solution |

TABLE 1-continued

| Prodrug type | mechanism of transformation | advantages | disadvantages |
|---|---|---|---|
| 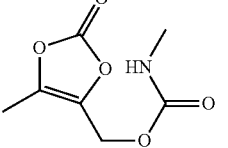<br>(oxodioxolenyl)methyl derivatives | base catalysis and/or enzymatic | also applicable to primary amines | |
| 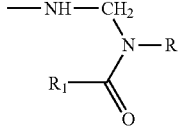<br>N-Mannich bases | base catalysis | lowers pKa up to 3 units | formation of formaldehyde low stability |
| 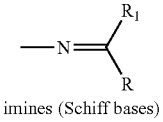<br>imines (Schiff bases) | pH activated | lowers pKa | easily hydrolyzed in aqueous solution |
| 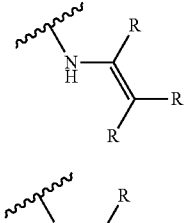<br>enamines and enaminones | chemical | lowers pKa improved lipophilicity | not stable enough at low pH |
| —N═N—<br>azo compounds | azo-reductases | possibility of targeting | only applicable to aromatic amines |
| 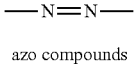 | enzymatic followed by spontaneous | possible to manipulate phys/chem characteristics | poor aqueous solubility in most cases |
| 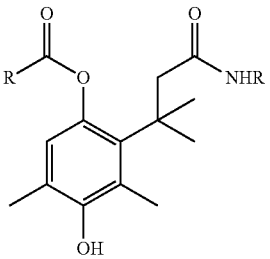<br>lactonization systems | | | |
| 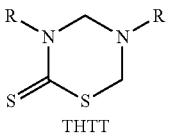<br>THTT | enzymatic and chemical | improved lipophilicity | only applicable to primary amines |

TABLE 1-continued

| Prodrug type | mechanism of transformation | advantages | disadvantages |
|---|---|---|---|
| R—NO$_2$ redox systems 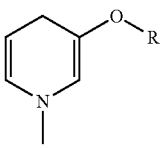 | chemical or enzymatic activation | possibility of targeting | oxidation in solid state |
| PEG | chemical and enzymatic activation | improved solubility | need association with other systems |

In some embodiments, the prodrug moiety may be selected from Table 2, as adapted from Larsen, in particular for a prodrug moiety to be attached to an oxygen, where R groups in a figure may be the same or different:

TABLE 2

| Functional group | Prodrug form | |
|---|---|---|
| —COOH | 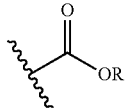 | Esters |
| | 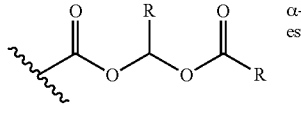 | α-Acyloxyalkyl esters |
| | 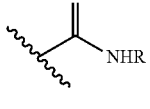 | Amides |
| —OH | 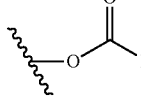 | Esters |
| | 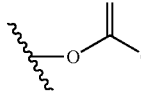 | Carbonate esters |
| | 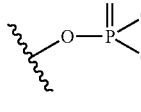 | Phosphate esters |
| | 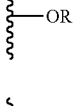 | Ethers |
| | 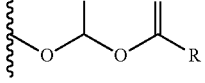 | α-Acyloxyalkyl ethers |

TABLE 2-continued

| Functional group | Prodrug form | |
|---|---|---|
| —SH | 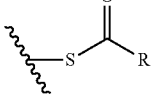 | Thioesters |

Figure 2:
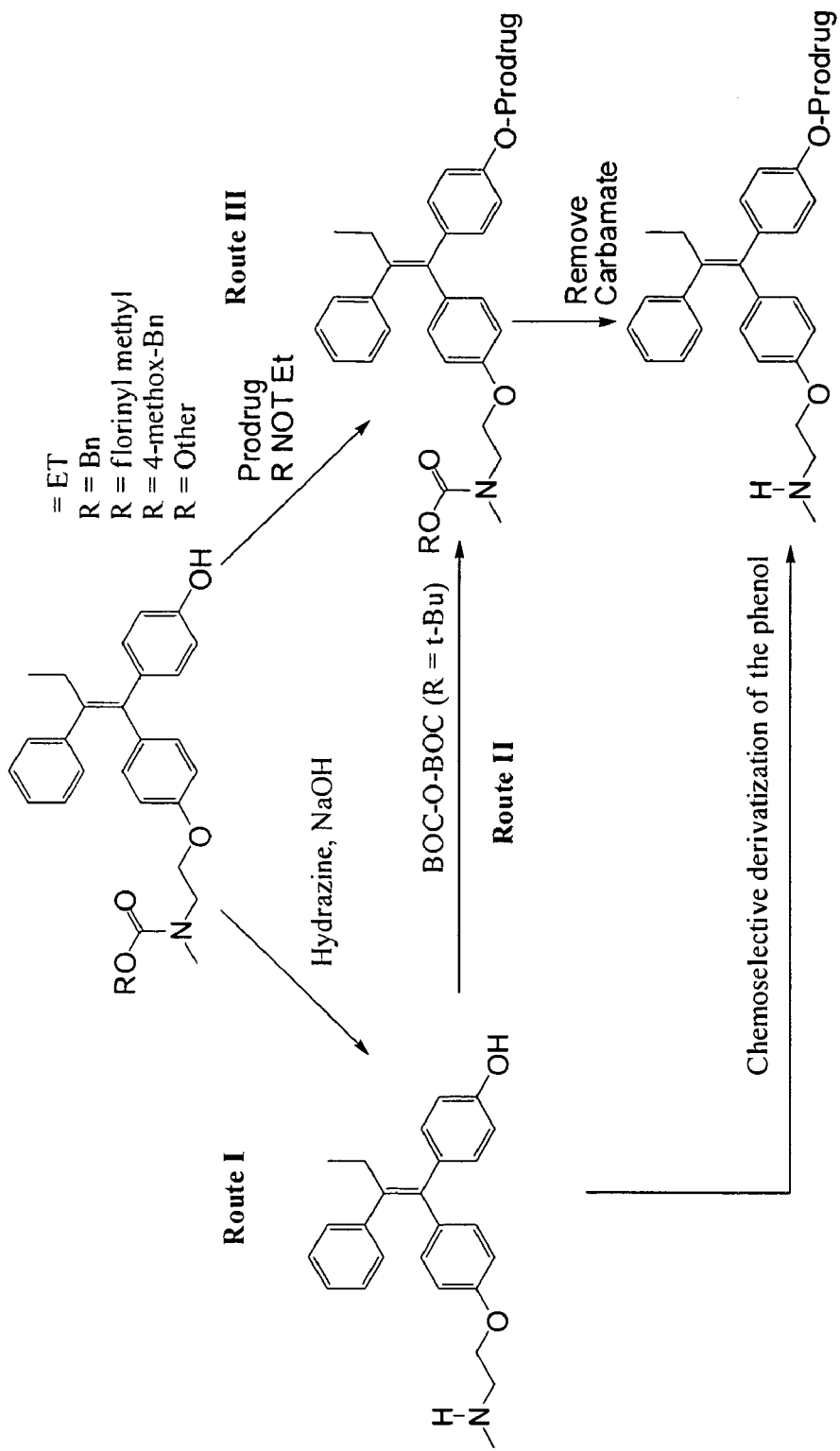
FIG. 2 shows synthetic options for access to O-Pro-compounds.
Figure 3:
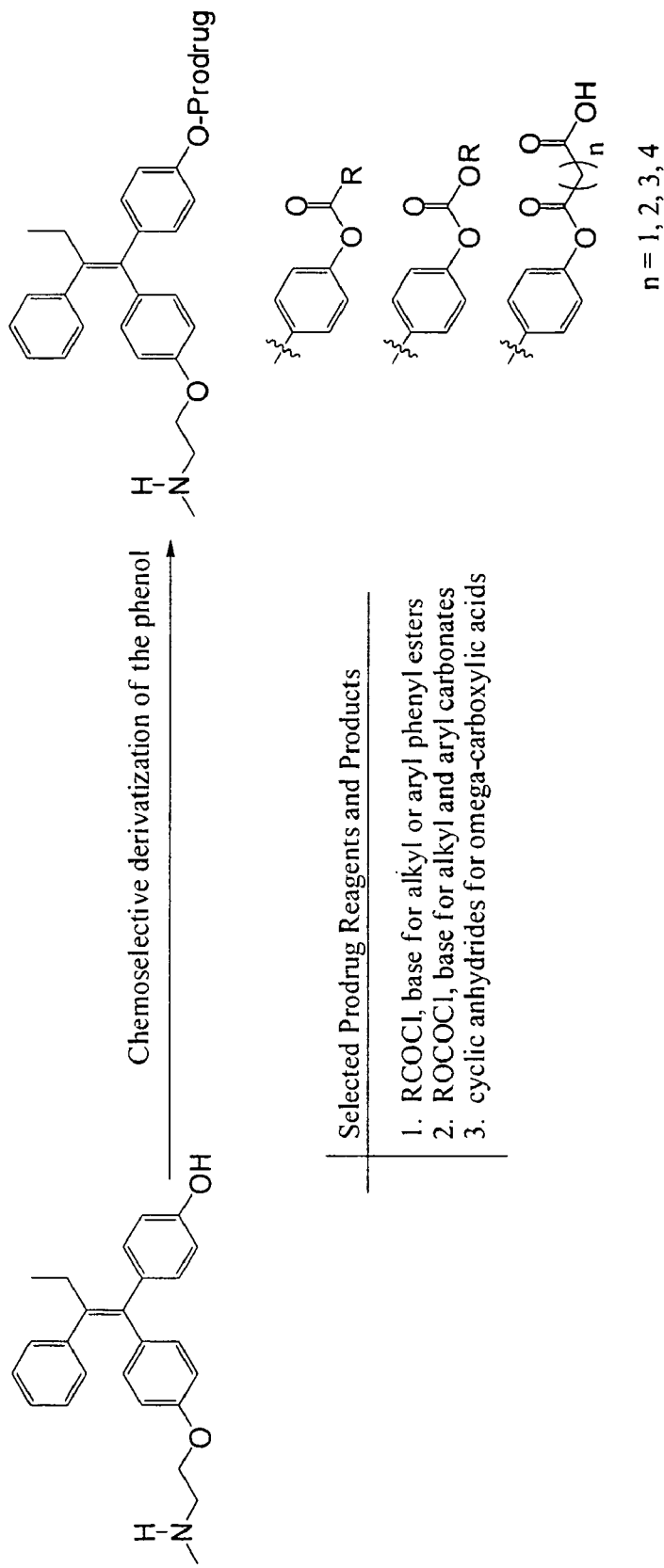
FIG. 3 shows a direct activation of the phenol-OH.
Figure 4:
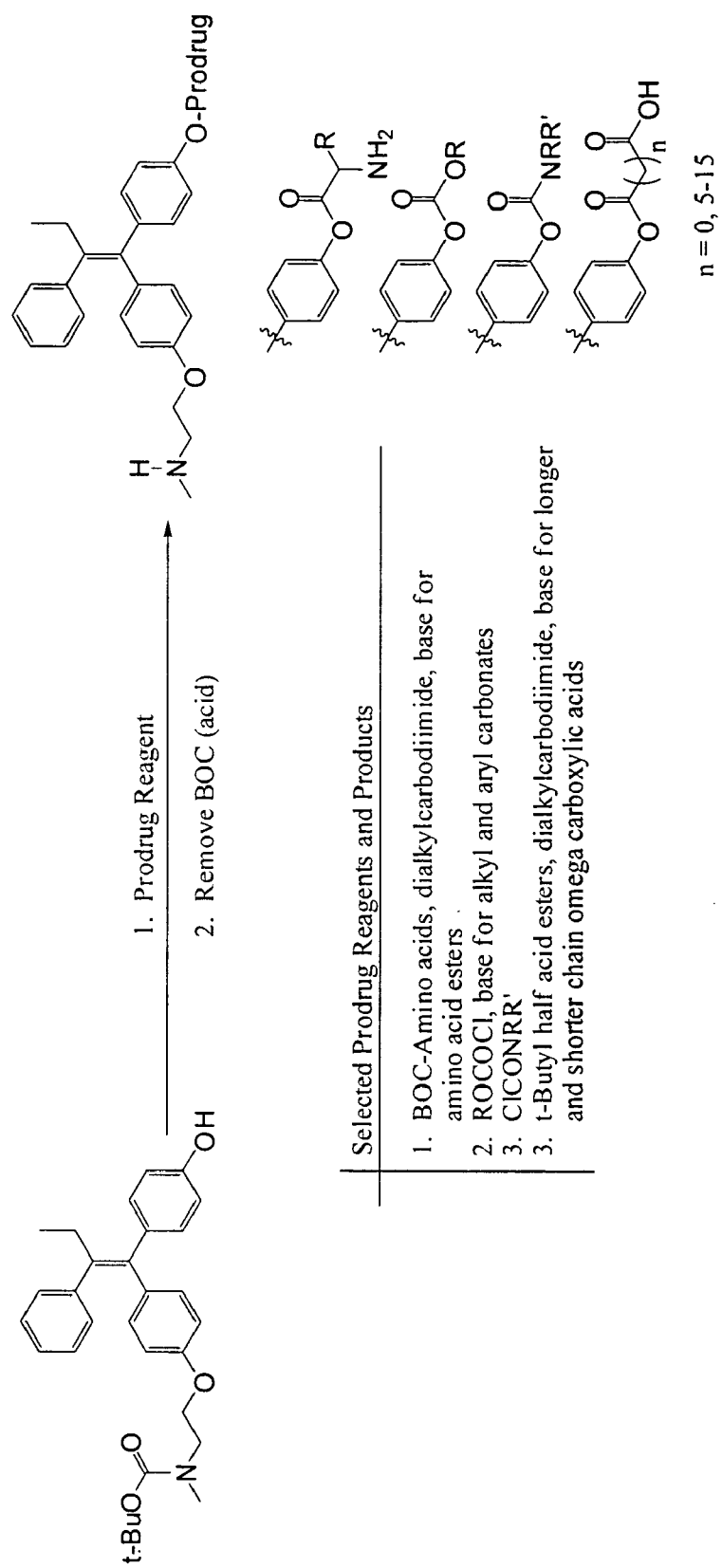
FIG. 4 shows a route to O-Pro-compound via a protected amine.
Figure 5:
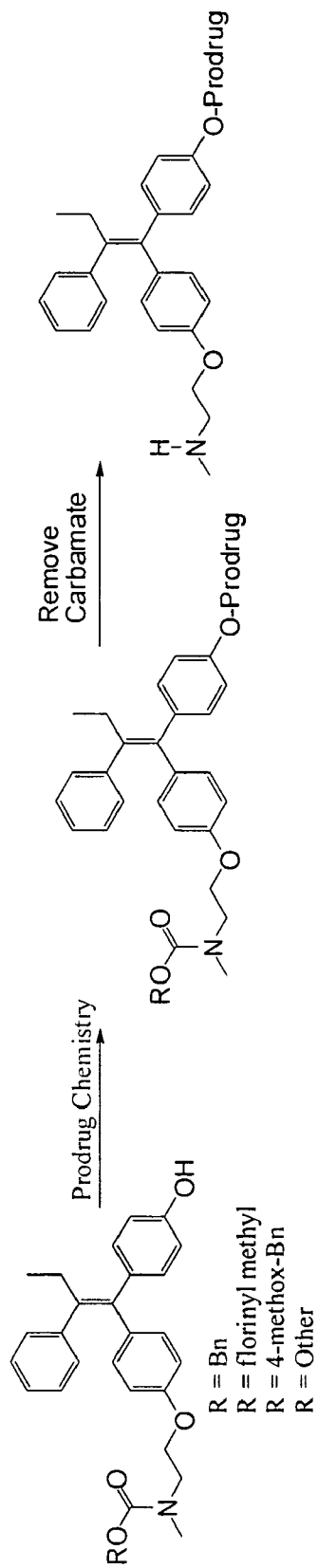
FIG. 5 shows additional options for access to O-Pro-compounds.
Figure 6:
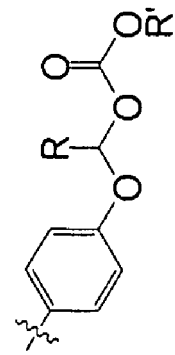
FIG. 6 shows additional classes of phenol prodrugs.
Figure 6:
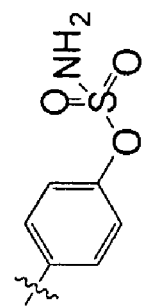
Figure 6:
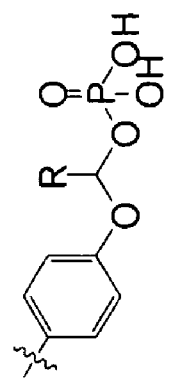
Figure 7:
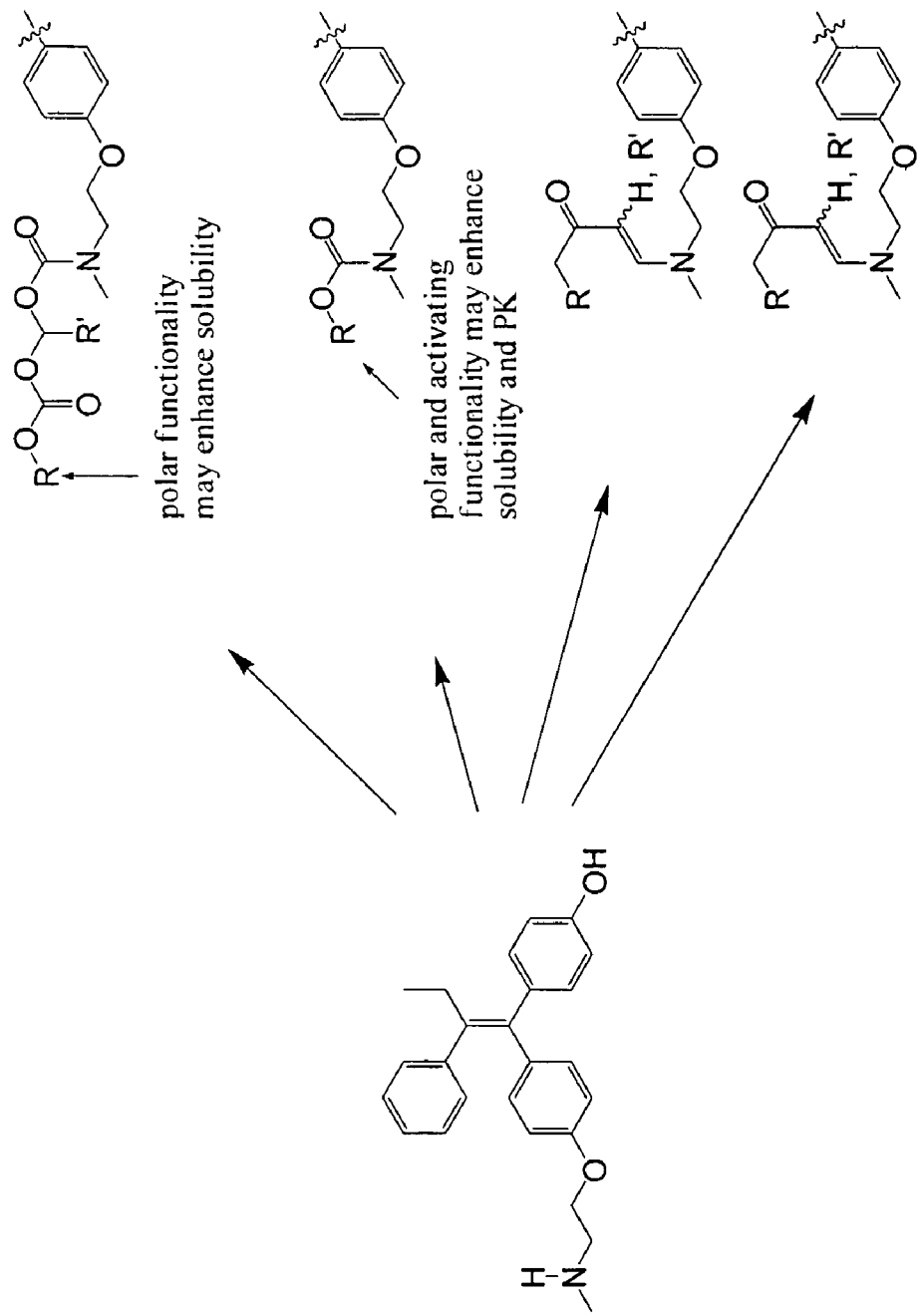
FIG. 7 shows proposed synthetic options for access to N-Pro-endoxifens.
Figure 8:
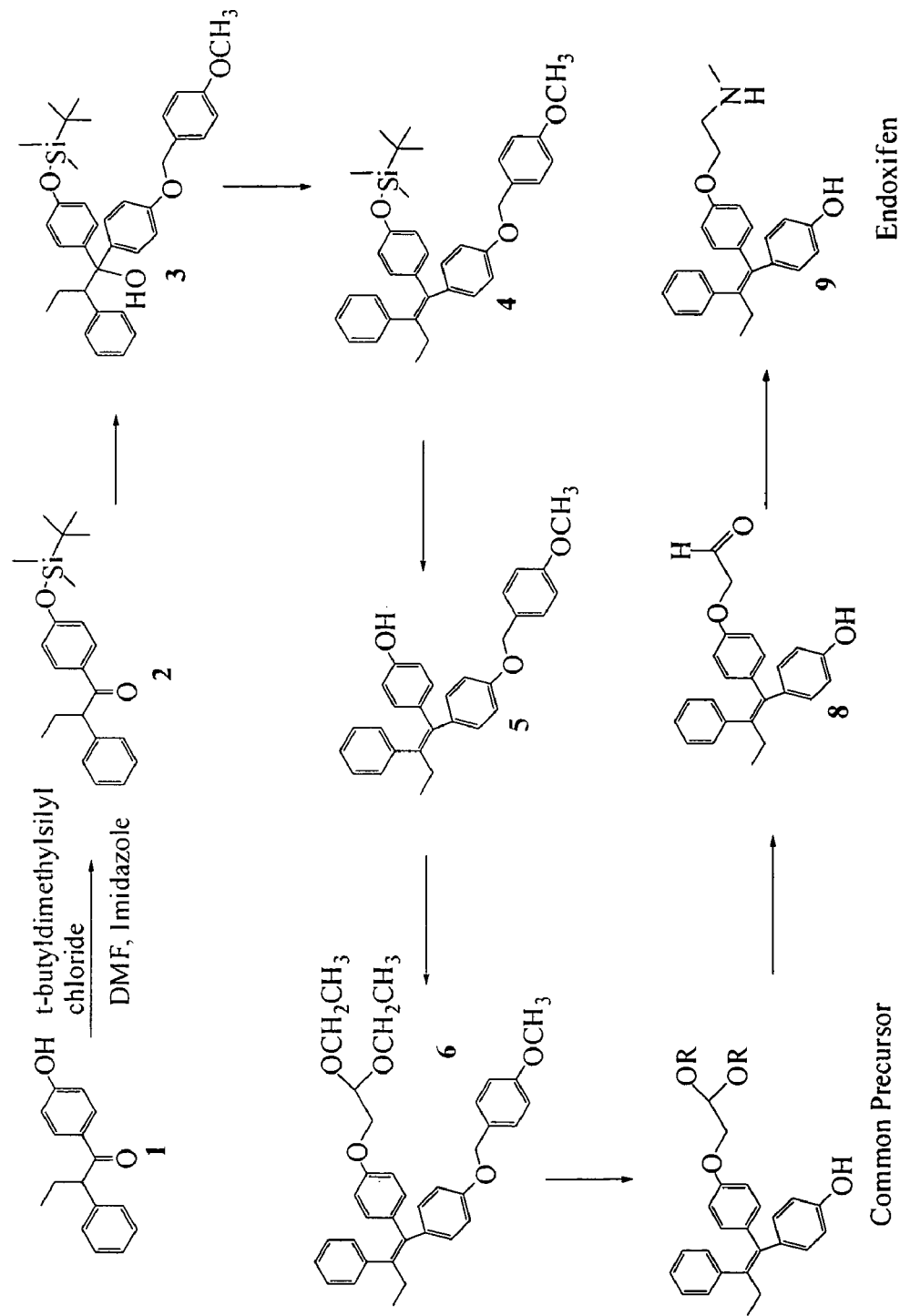
FIG. 8 shows a synthetic scheme for endoxifen via an aldehyde precursor. The —OR groups form an acetal, and may be, for example, —OMe or —OEt.
Figure 9:
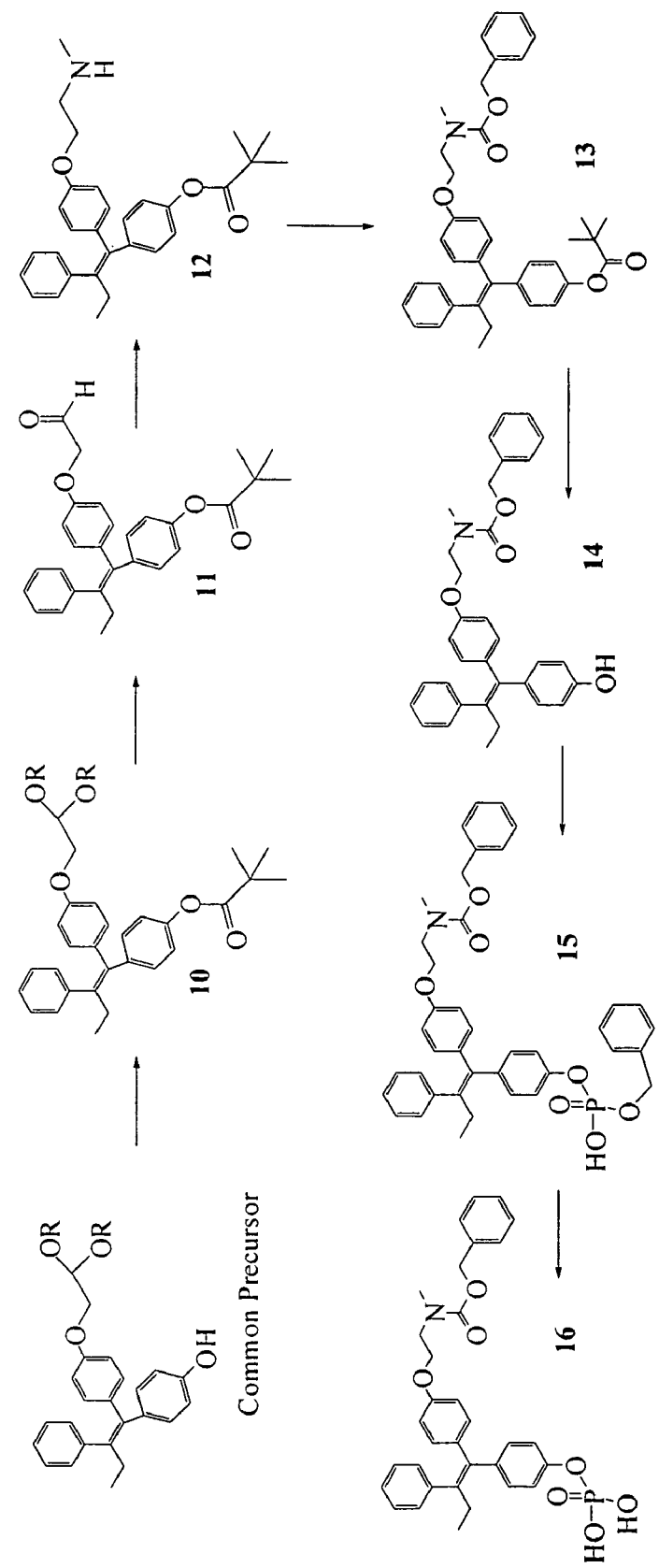
FIG. 9 shows a synthetic scheme of a pivalate ester and an endoxifen phosphate via a common precursor. The —OR groups form an acetal, and may be, for example, —OMe or —OEt.

In various embodiments, a prodrug moiety may be adapted from Tables 1 or 2, or from FIGS. 2-6. Such prodrugs may include R groups (including $R_1$, $R_2$, etc.) as defined above for Formulas I and II. The synthesis of prodrugs according to the invention may be adapted from the Examples below, from FIGS. 2-6, and from standard transformations available to the practitioner in the art. For example, see Simplicio et al., "Prodrugs for Amines," Molecules, vol. 13, iss. 3, pp. 519-547, March 2008, available from the internet at <<http://www.mdpi.org>>; see also Larsen, C. S., et al., "Chapter 14: Design and application of prodrugs" from Textbook of Drug Design and Discovery, Third Edition, edited by Krogsgaard-Larsen, P. et al., pages 410-458, 2002. See also March, J., Advanced Organic Chemistry: Reactions, Mechanisms, and Structure, Fourth Edition, John Wiley & Sons, Inc., publishers, 1992; Greene, T. W., Protective Groups in Organic Synthesis, John Wiley & Sons, Inc., publishers, 1981; and Larock, R. C., Comprehensive Organic Transformations: A Guide to Functional Group Preparations, John Wiley & Sons, Inc., publishers, November 1999. The contents of each publication are incorporated by reference. Substituents for the generic groups in Tables 1 and 2 may be as understood in the art, including substituted or unsubstituted derivatives thereof. In one embodiment, any R group (including $R_1$, $R_2$, etc.) in Table 1 or 2 is independently a $C_1$-$C_6$ alkyl group.

As discussed above, the term "prodrug" means a compound with a temporary modification of a functional group of a drug in order to improve the pharmaceutical utility of the drug. Prodrug may refer to the entire compound, or it may refer to the chemical modification, in the context of a prodrug moiety being the chemical modification. In some embodiments, the functional group of the drug is a handle for the introduction of a moiety that confers on the new entity some desirable characteristic. In other embodiments, the prodrug moiety is intimately connected with the pharmaceutical deficiency of the parent drug, and the presence of the prodrug moiety directly addresses the deficiency. In some embodiments, prodrugs rely on in vivo enzymatic activation for conversion to active form of the drug for example by cleavage of the prodrug moiety by an enzyme. In other embodiments, prodrugs rely on physiological chemical conditions for release of the drug, for example through a change in pH. The benefits of a prodrug are not limited to improved in vivo benefits compared to the parent drug, but may also include improved processing or storage characteristics or economic considerations prior to administration to the patient. In various embodiments, the advantages of the prodrug moiety may be selected from the group consisting of improved biomembrane passage and bioavailability (including improved oral absorption, dermal absorption, ocular absorption, gastro-intestinal absorption, and/or reduced first-pass metabolism), site-directed drug delivery, site-specific bioactivation, improvement of drug formulation, and combinations thereof.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc. Pharmaceutically acceptable non-toxic salts may include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylaminoethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, p-toluenesulfonic, methanesulfonic acid, oxalic, tartaric, mandelic, and the like. Salts of the invention include amine salts formed by the protonation of an amino group with inorganic acids such as hydrochloric acid, hydrobromic acid, hydroiodic acid, sulfuric acid, phosphoric acid, and the like. Salts of the invention also include amine salts formed by the protonation of an amino group with suitable organic acids, such as p-toluenesulfonic acid, acetic acid, and the like. Additional salt-forming excipients which are contemplated for use in the practice of the present invention are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference.

5.7 Embodiments

Therapy

Any therapy (e.g., chemotherapies, radiation therapies, hormonal therapies, and/or biological therapies/immunotherapies) which is known to be useful, or which has been used or is currently being used for the prevention, treatment, management or amelioration of cancer or one or more symptoms thereof can be used in accordance with the invention, and may be combined with any of the compositions described herein, and may encompass the other active ingredient described for some of the combination therapies herein.

In some embodiments, the anti-cancer agents contemplated in the methods and compositions of the present invention, which can be administered in combination with the compositions of the present invention include, but are not limited to doxorubicin, epirubicin, the combination of doxorubicin and cyclophosphamide (AC), the combination of cyclophosphamide, doxorubicin and 5-fluorouracil (CAF), the combination of cyclophosphamide, epirubicin and 5-fluorouracil (CEF), herceptin, tamoxifen, the combination of tamoxifen and cytotoxic chemotherapy, taxanes (such as docetaxel and paclitaxel). In a further embodiment, the combinations of the invention can be administered with taxanes plus standard doxorubicin and cyclophosphamide for adjuvant treatment of node-positive, localized breast cancer.

In one embodiment, the dose of doxorubicin hydrochloride (i.v.) is 60-75 mg/m$^2$ on day 1 of treatment. In another embodiment, the dose of epirubicin (i.v.) is 100-120 mg/m$^2$ on day 1 of each cycle or divided equally and given on days 1-8 of the treatment cycle. In yet another embodiment, the dose of docetaxel (i.v.) is 60-100 mg/m$^2$ over 1 hour. In another embodiment, the dose of paclitaxel (i.v.) is 175 mg/m$^2$ over 3 hours.

The present invention can be used to treat a patient with any type of breast cancer. Breast cancers may include carcinoma in situ, infiltrating (or invasive) ductal carcinoma, infiltrating (or invasive) lobular carcinoma, medullary carcinoma, colloid carcinoma, tubular carcinoma, and inflammatory carcinoma.

In addition to the different types of breast cancer, there are also different stages of breast cancer, referred to as stages 0-IV. The system most often used to describe the growth and spread of breast cancer is the TNM staging system, also known as the American Joint Committee on Cancer (AJCC) system. In TNM staging, information about the tumor, nearby lymph nodes, and distant organ metastases is combined and a stage is assigned to specific TNM groupings. The grouped stages are described using Roman numerals from I to IV. The clinical stage is determined by results from physical examination and tests. The pathologic stage includes the findings of the pathologist after surgery. Most of the time, pathologic stage is the most important stage because usually the cancer isn't known to have spread to lymph nodes until the pathologist examines them under the microscope. In the TNM staging system, T stands for the size of the cancer (measured in centimeters; 2.54 centimeters 1 inch); N stands for spread to lymph nodes in the area of the breast, and M is for metastasis (spread to distant organs of the body).

The T category describes the original (primary) tumor. Tis: Tis is used only for carcinoma in situ or noninvasive breast cancer such as ductal carcinoma in situ, (DCIS) or lobular carcinoma in situ (LCIS). T1: The cancer is 2 cm in diameter (about ¾ inch) or smaller. T2: The cancer is more than 2 cm but not more than 5 cm in diameter. T3: The cancer is more than 5 cm in diameter. T4: The cancer is any size and has spread to the chest wall, the skin, or lymphatics.

The N category is based on which of the lymph nodes near the breast, if any, are affected by the cancer. N0: The cancer has not spread to lymph nodes. N1: The cancer has spread to lymph nodes under the arm on the same side as the breast cancer. Lymph nodes have not yet attached to one another or to the surrounding tissue. N2: The cancer has spread to lymph nodes under the arm on the same side as the breast cancer and are attached to one another or to the surrounding tissue or enlarged. Or, the cancer can be seen to have spread to the internal mammary lymph nodes (next to the sternum), but not to the lymph nodes under the arm. N3: The cancer has spread to lymph nodes above or just below the collarbone on the same side as the cancer, and may or may not have spread to lymph nodes under the arm. Or, the cancer has spread to internal mammary lymph nodes and lymph nodes under the arm, both on the same side as the cancer.

M categories: The M category depends on whether the cancer has spread to any distant tissues and organs. M0: No distant cancer spread. M1: Cancer has spread to distant organs.

There are different types of staging. Clinical staging estimates how much cancer there is based on the results of the physical exam, imaging tests (x-rays, CT scans, etc.) and sometimes biopsies of affected areas. For certain cancers the results of other tests, such as blood tests, are also used in staging. Pathologic staging can only be done on patients who have had surgery to remove or explore the extent of the cancer. It combines the results of clinical staging (physical exam, imaging tests, etc.) with the results from the surgery. In some cases, the pathologic stage may be different from the clinical stage (for example, if the surgery shows the cancer is more extensive than it was previously thought to be). Restaging is sometimes used to determine the extent of the disease if a cancer recurs (comes back) after treatment.

In one embodiment, the methods and compositions of the present invention are used to treat patients with stage I breast cancer.

In one embodiment, the methods and compositions of the present invention are used to treat patients with stage II breast cancer.

In one embodiment, the methods and compositions of the present invention are used to treat patients with stage III breast cancer.

In one embodiment, the methods and compositions of the present invention are used to treat patients with stage IV breast cancer, i.e. patients with metastatic cancer.

In another embodiment, the patient having breast cancer has already failed other treatment regimens such as chemotherapy.

In one embodiment, the methods and pharmaceutical compositions of the present invention may be used to prevent the development of a cancer, particularly in an individual at higher risk than average to develop such cancer than other individuals, or to treat a patient afflicted with breast cancer.

There are a number of ways to assess an individual's risk for breast cancer, and any means of risk assessment is contemplated by the present invention as determining which subjects are at risk for breast cancer and can undergo treatment via the methods and compositions of the present invention. The invention contemplates treatment for individuals with a higher than average lifetime risk for breast cancer, the average being about one in eight women in the U.S.

The invention provides methods treating asymptomatic patients who have a likelihood of benefiting from therapeutic treatment of breast cancer. The asymptomatic patients can comprise patients in any of the many high risk groups for breast cancer. The high risk groups can include e.g. patients with a family history of breast cancer, patients of increasing age (e.g., patients 40 years of age or older), menopausal patients, patients having at least one high risk parity factor (e.g. early start of menses, late onset of menopause, no pregnancies, or late-age pregnancy), patients having high risk gene status (e.g. patients testing positive for a mutation in BRCA1 or BRCA2 genes, or others, as described below), patients having at least one previous breast biopsy (benign or otherwise), patients having a previous diagnosis of breast cancer, and patients having any other risk factor for breast cancer. Other risk factors are continually being defined and can include such considerations, as geographic location (e.g. where women living in a particular region have been found to have a higher incidence of breast cancer). Diet is also thought to play a role in breast cancer risk; specifically women who include more fat in their diet may be more likely to develop breast cancer (see Kniget et al. Cancer Epidemiol Biomarkers Prey 8(2):123-8, 1999).

The Gail model is a common means of determining risk for breast cancer, and was developed based on the Breast Cancer Detection Demonstration Project (see Gail, M. et al, J Natl Cancer Inst., 1989. 81: p. 1879-86). The risk factors used in the Gail model are age, age at menarche, age at first live birth, number of previous breast biopsies, number of first-degree relatives with breast cancer. These risk factors are broadly consistent with those selected from other large population-based studies. A revised Gail model also incorporates race, presence of atypical hyperplasia on breast biopsy, and 1987 population rates of breast cancer and death from other causes.

Another commonly used prediction model is the Claus model, based on the Cancer and Steroid Hormone Study (see Claus E. et al., Cancer, 1994. 73: 643-51) and incorporates more extensive information about family history. The Claus model provides individual estimates of breast-cancer risk according to decade from 29-79 years of age. It takes into account factors such as the number of first-degree and number of second-degree relatives with breast cancer, as well as different combinations of different degree relatives with breast cancer.

The invention also contemplates treatment for early stages of cancer, for recurrent cancer, and for those in remission from cancer.

The present invention also encompasses treatment for subjects with markers for breast cancer, including, but not limited to having mutations or other alterations in the genes, BRCA1, BRCA2, P53, P65, ATM, or pS2, or a changed ratio of the expression of the genes HOXB13 and IL17BR, amplification of the AIB1/pCIP coactivator gene, overproduction of HER2 protein and/or gene, and alterations in levels of hormones, such as estrogen and progesterone, or their receptors.

Markers can also include neoplastic ductal epithelial cells, transforming growth factor-β, carcinoma embryonic antigen (CEA), prostate specific antigen (PSA), Erb B2 antigen, gross cystic disease fluid protein-15 (GCDFP-15), lactose dehydrogenase (LDH), measured in the ductal fluid, or a chromosomal abnormality in the ductal epithelial cells. Where the marker is neoplastic ductal epithelial cells, the cells can be at a stage including hyperplasia, atypical hyperplasia, low grade ductal carcinoma in situ (LG-DCIS), high grade ductal carcinoma in situ (HG-DCIS) or invasive carcinoma. The present invention encompasses providing the pharmaceutical compositions described herein to treat subjects with any of the described markers, and also to prevent the progression from DCIS and from atypical hyperplasia to breast cancer.

The compositions of the invention may be administered either prior to or following surgical removal of primary tumors and/or treatment such as administration of radiotherapy or conventional chemotherapeutic drugs.

The methods and compositions of the present invention may be used advantageously in combination with any other treatment regimen for breast cancer. Treatments for breast cancer are well known in the art and continue to be developed. Treatments include but are not limited to surgery, including axillary dissection, sentinel lymph node biopsy, reconstructive surgery, surgery to relieve symptoms of advanced cancer, lumpectomy (also called breast conservation therapy), partial (segmental) mastectomy, simple or total mastectomy, modified radical mastectomy, and radical mastectomy; immunotherapy, e.g. using Herceptin™ (trastuzumab), an anti-HER2 humanized monoclonal antibody developed to block the HER2 receptor; bone marrow transplantation; peripheral blood stem cell therapy; bisphosphonates; additional chemotherapy agents; radiation therapy; acupressure; and acupuncture. Any combination of therapies may be used in conjunction with the present invention.

The methods and compositions comprising the combination therapies described herein may also be used to reduce the proliferation of cancer cells, increase the death of cancer cells or, reduces the size of a tumor or spread of a tumor in a subject. It is contemplated by the present invention that the combination therapies described herein may reduce the size of a tumor or the spread of a tumor in a subject by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as PBS. In some embodiments, the combination therapies described herein may increase survival by 1 month, 2 months, 6 months, 1 year, 2 years, 3 years, 4 years, 5 years, 6 years, 7 years, 8 years, 9 years, 10 years, or more, it may render the subject disease-free, or it may prevent the progression from DCIS or atypical hyperplasia to breast cancer.

6. EXAMPLES

The following series of Examples are presented for purposes of illustration and not by way of limitation on the scope of the invention. Isomerization between E and Z isomers for intermediates and final products may occur. As such, mixtures of E and Z isomers are envisioned, and may be retained or, if desired, specific isomers may be enriched to the point of purity.

Example 1

6-hydroxyhexyl bromoacetamide

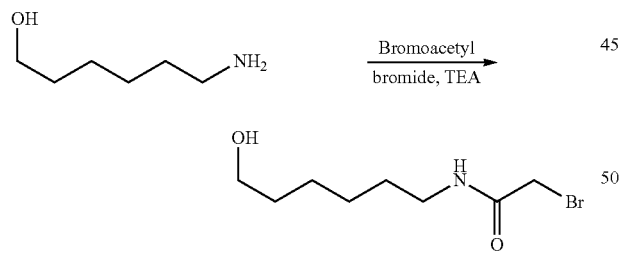

6-aminohexanol is dissolved in dichloromethane. This solution may be cooled in an ice water bath. The solution is the treated with neat bromoacetyl bromide or a solution of this reagent in dichloromethane. The progress of the reaction is followed by TLC. When the reaction is complete, the mixture is washed with dilute hydrochloric acid, dilute sodium bicarbonate and water. The organic layer is then dried over sodium sulfate or other suitable desiccant. The dried suspension is then filtered and concentrated under reduced pressure to afford 6-hydroxyhexyl bromoacetamide among other products.

Example 2

(E)-4-(2-phenyl-1-(4-(triisopropylsilyloxy)phenyl)but-1-enyl)phenol

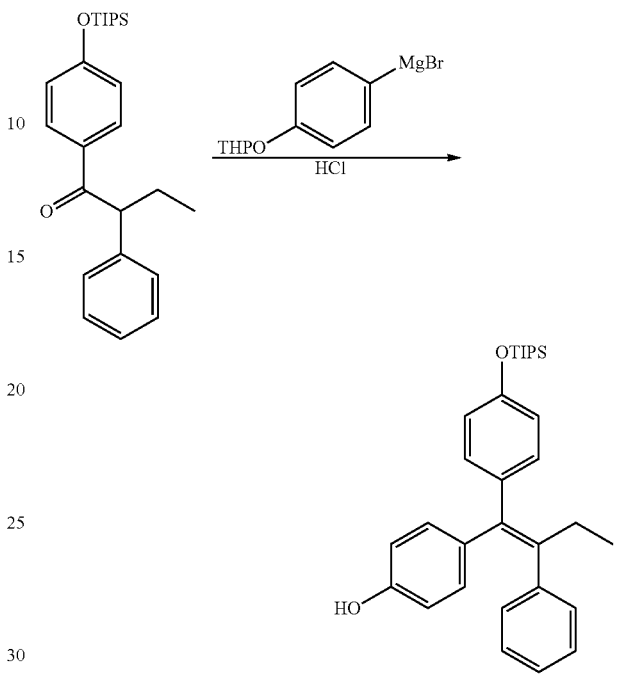

The THP ether of 4-bromophenol is dissolved in ether. To this solution is added magnesium metal. The mixture is warmed gently to initiate the reaction. When the starting material has been consumed (TLC), the mixture is cooled in an ice bath and the ketone is added. After the reaction has gone to completion (TLC), the reaction is quenched by slow addition of ethanolic HCl. The mixture is stirred until the reaction is complete (TLC). Excess acid is neutralized (ph ca. 7, pH test paper) with dilute sodium hydroxide solution. The organic phase is separated and washed with brine. The aqueous phase is washed with ether. The phases are then separated. The organic phases are combined, dried over sodium sulfate, filtered and concentrated to afford (E)-4-(2-phenyl-1-(4-(triisopropylsilyloxy)phenyl)but-1-enyl)phenol among other products.

Example 3

(E)-N-(6-hydroxyhexyl)-2-(4-(2-phenyl-1-(4-(triisopropylsilyloxy)phenyl)but-1-enyl)phenoxy)acetamide

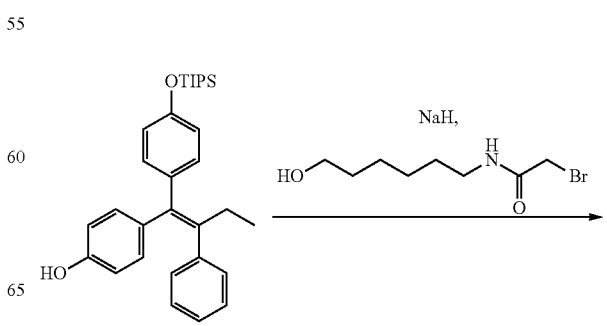

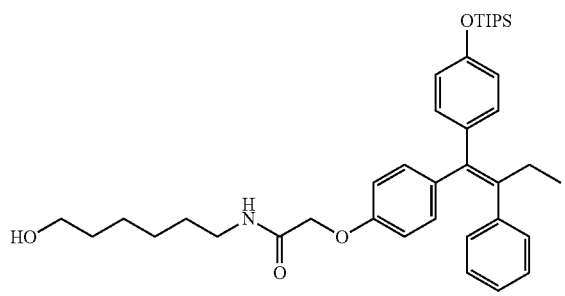

(E)-4-(2-phenyl-1-(4-(triisopropylsilyloxy)phenyl)but-1-enyl)phenol from reaction 2 is dissolved in THF. The solution is then treated with sodium hydride (1 equiv). To this solution is added 6-hydroxyhexyl bromoacetamide (from reaction 1). The mixture is stirred until the reaction is complete (TLC). The reaction is then quenched by addition of a small quantity of water. After the reaction is stirred for several minutes, solid sodium sulfate is added. The mixture is the filtered and concentrated under reduced pressure to afford (E)-N-(6-hydroxyhexyl)-2-(4-(2-phenyl-1-(4-(triisopropylsilyloxy)phenyl)but-1-enyl)phenoxy)acetamide among other products.

Example 4

(Z)-2-(4-(1-(4-hydroxyphenyl)-2-phenylbut-1-enyl)phenoxy)-N-(6-(4,4,5,5,5-pentafluoropentylthio)hexyl)acetamide (E)-N-(6-hydroxyhexyl)-2-(4-(2-phenyl-1-(4-(triisopropylsilyloxy)phenyl)but-1-enyl)phenoxy)acetamide from reaction 3 is dissolved in dichloromethane. To this solution are added triethyl amine and p-toluenesulfonyl chloride in that order. The solution is stirred until the reaction is complete (TLC). 5,5,6,6,6-pentafluorohexanethiol is then added and the mixture stirred until the reaction is complete (TLC). When the reaction is complete, the mixture is washed with dilute hydrochloric acid, dilute sodium bicarbonate and water. The organic layer is the dried over sodium sulfate or other suitable desiccant. The dried suspension is then filtered and concentrated under reduced pressure to afford (Z)-2-(4-(1-(4-hydroxyphenyl)-2-phenylbut-1-enyl)phenoxy)-N-(6-(4,4,5,5,5-pentafluoropentylthio)hexyl)acetamide among other products.

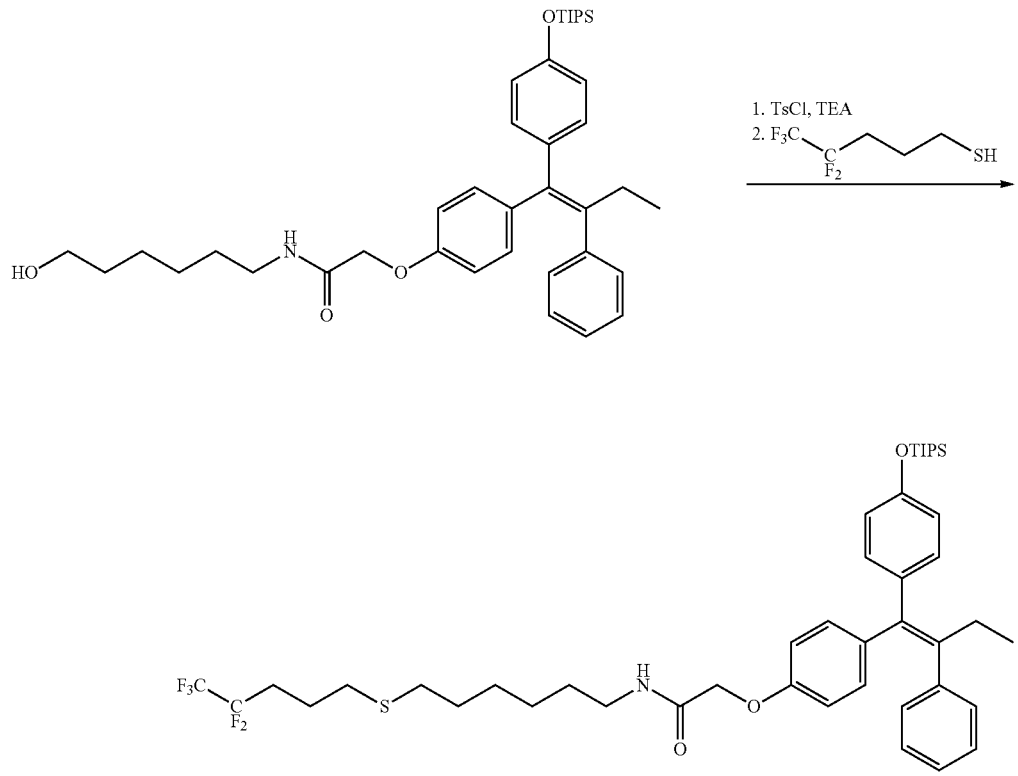

Example 5

(E)-6-(4,4,5,5,5-pentafluoropentylthio)-N-(2-(4-(2-phenyl-1-(4-(triisopropylsilyloxy)phenyl)but-1-enyl)phenoxy)ethyl)hexan-1-amine

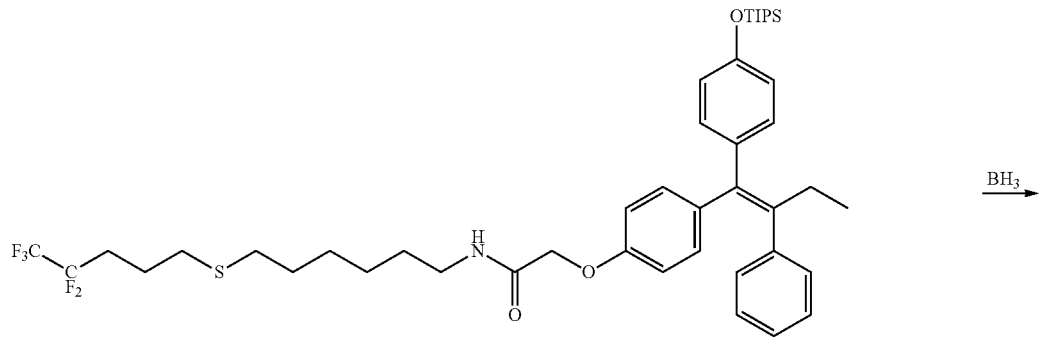

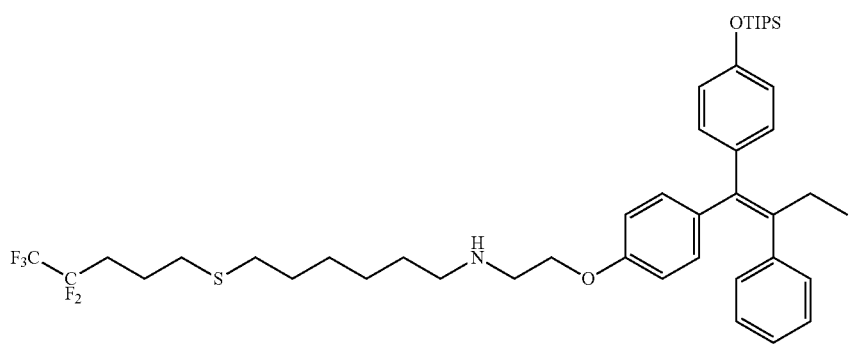

(Z)-2-(4-(1-(4-hydroxyphenyl)-2-phenylbut-1-enyl)phenoxy)-N-(6-(4,4,5,5,5-pentafluoropentylthio)hexyl)acetamide from reaction 4 is dissolved in THF. To this solution is added borane THF complex or other suitable reducing agent. The mixture is stirred until the reaction is complete (TLC). A small quantity of acetone is then added. The mixture is then diluted with water and extracted with ethyl acetate. The combined organic layers are washed with brine, dried over sodium sulfate, filtered and concentrated to afford (E)-6-(4,4,5,5,5-pentafluoropentylthio)-N-(2-(4-(2-phenyl-1-(4-(triisopropylsilyloxy)phenyl)but-1-enyl)phenoxy)ethyl)hexan-1-amine among other products.

Example 6

(Z)-4-(1-(4-(2-(6-(4,4,5,5,5-pentafluoropentylthio)hexylamino)ethoxy)phenyl)-2-phenylbut-1-enyl)phenol

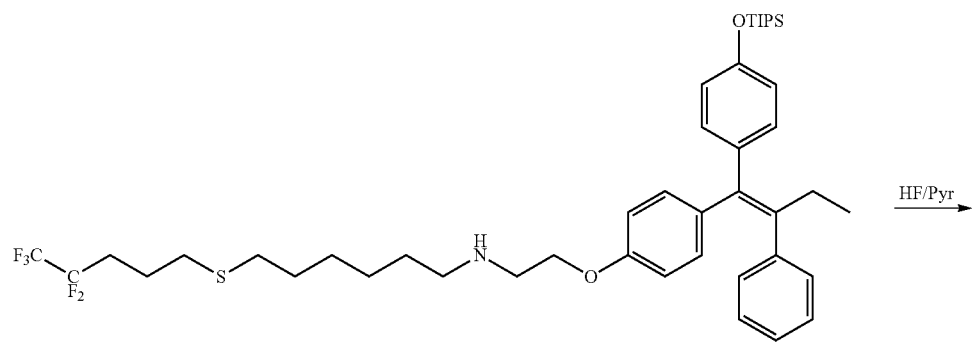

-continued

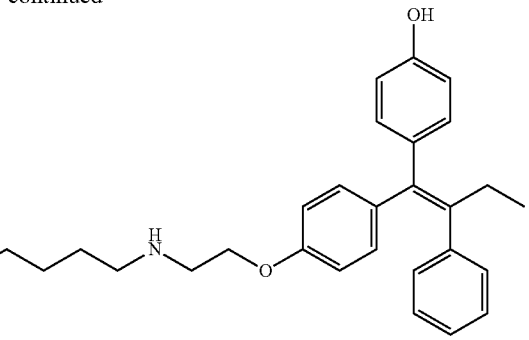

(E)-6-(4,4,5,5,5-pentafluoropentylthio)-N-(2-(4-(2-phenyl-1-(4-(triisopropylsilyloxy)phenyl)but-1-enyl)phenoxy)ethyl)hexan-1-amine from reaction 6 is dissolved in acetonitrile. To this solution is added HF/pyridine complex. The mixture is stirred until the reaction is complete (TLC). When the reaction is complete, the mixture is washed with dilute hydrochloric acid, dilute sodium bicarbonate and water. The aqueous layers are extracted with ethyl acetate. The combined organic extracts are dried over sodium sulfate, filtered, and concentrated under reduced pressure to afford (Z)-4-(1-(4-(2-(6-(4,4,5,5,5-pentafluoropentylthio)hexylamino)ethoxy)phenyl)-2-phenylbut-1-enyl)phenol among other products.

Example 7

(Z)-4-(1-(4-(2-(6-(4,4,5,5,5-pentafluoropentylsulfinyl)hexylamino)ethoxy)phenyl)-2-phenylbut-1-enyl)phenol (Z)-4-(1-(4-(2-(6-(4,4,5,5,5-pentafluoropentylthio)hexylamino)ethoxy)phenyl)-2-phenylbut-1-enyl)phenol from the previous reaction is dissolved in ethyl acetate and acetic acid. To this solution is added hydrogen peroxide solution in water. The mixture is stirred until the reaction is complete (TLC). Excess hydrogen peroxide is destroyed by addition of sodium sulfite solution in water. The phases are separated and the aqueous phase is washed with ethyl acetate. The combined organic phases are dried over sodium sulfate, filtered and concentrated under reduced pressure to afford (Z)-4-(1-(4-(2-(6-(4,4,5,5,5-pentafluoropentylsulfinyl)hexylamino)ethoxy)phenyl)-2-phenylbut-1-enyl)phenol among other products.

Example 8

The same sequence of reactions as described in reactions 1-5 above using 5-aminopentanol in step 1 to furnish (E)-4-(1-(4-(2-(5-(4,4,5,5,5-pentafluoropentylsulfinyl)pentylamino)ethoxy)phenyl)-2-phenylbut-1-enyl)phenol among other products.

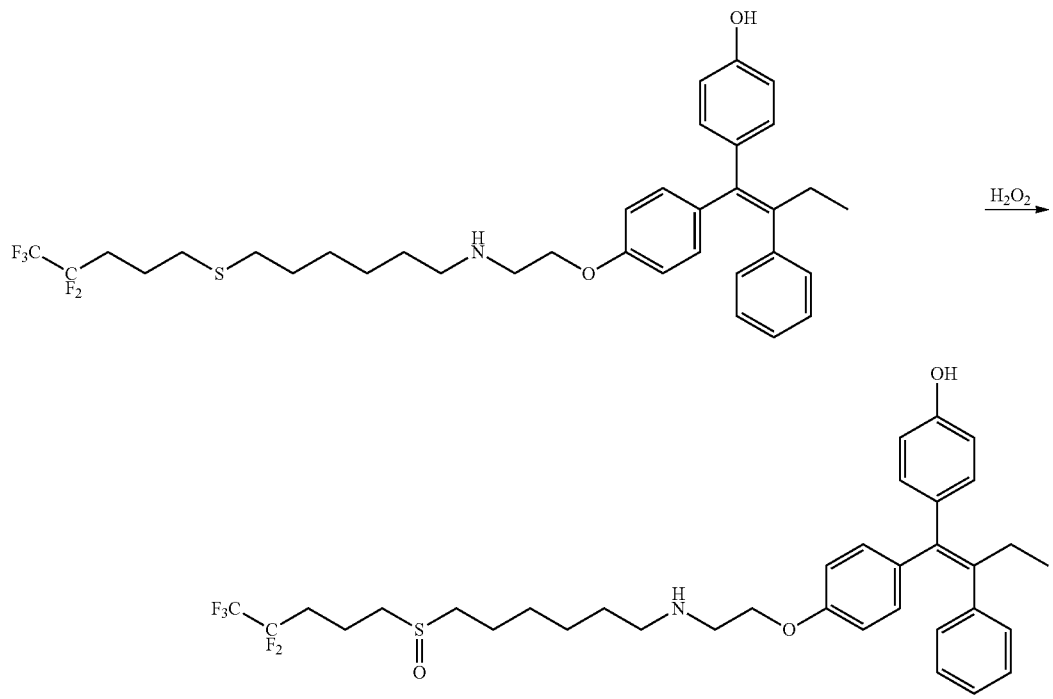

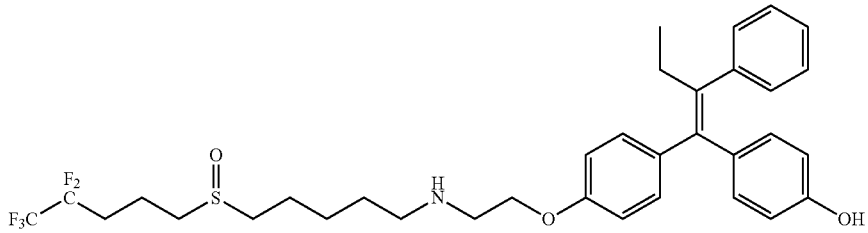

Example 9

The same sequence of reactions as described in reactions 1-5 above using 4-aminobutanol in step 1 to furnish (E)-4-(1-(4-(2-(4-(4,4,5,5,5-pentafluoropentylsulfinyl)butylamino)ethoxy)phenyl)-2-phenylbut-1-enyl)phenol among other products.

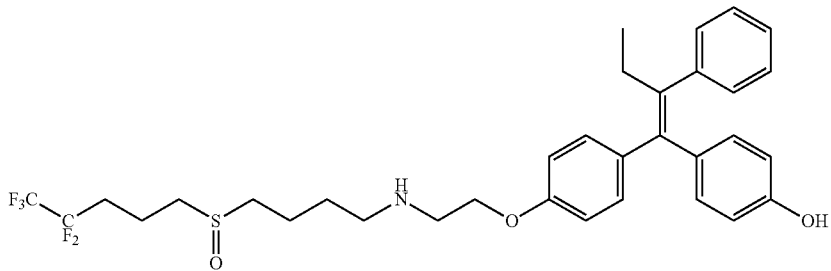

Example 10

The same sequence of reactions as described in reactions 1-5 above using 3-aminopropanol in step 1 to furnish (E)-4-(1-(4-(2-(3-(4,4,5,5,5-pentafluoropentylsulfinyl)propylamino)ethoxy)phenyl)-2-phenylbut-1-enyl)phenol among other products.

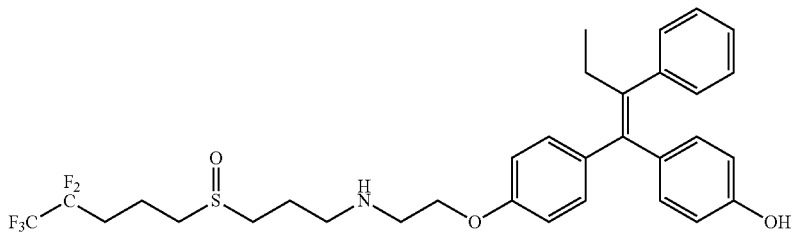

Example 11

The same sequence of reactions as described in reactions 1-5 above using 7-aminoheptanol in step 1 to furnish (E)-4-(1-(4-(2-(7-(4,4,5,5,5-pentafluoropentylsulfinyl)heptylamino)ethoxy)phenyl)-2-phenylbut-1-enyl)phenol among other products.

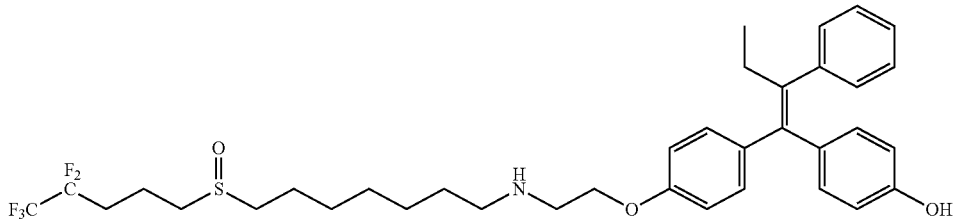

Example 12

The same sequence of reactions as described in reactions 1-5 above using 8-aminooctanol in step 1 to furnish (E)-4-(1-(4-(2-(8-(4,4,5,5,5-pentafluoropentylsulfinyl)octylamino)ethoxy)phenyl)-2-phenylbut-1-enyl)phenol among other products.

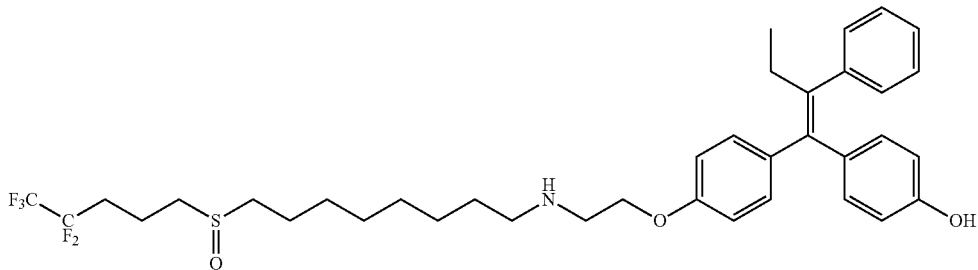

Example 13

The same sequence of reactions as described in reactions 1-5 above using 9-aminononanol in step 1 to furnish (E)-4-(1-(4-(2-(9-(4,4,5,5,5-pentafluoropentylsulfinyl)nonylamino)ethoxy)phenyl)-2-phenylbut-1-enyl)phenol among other products.

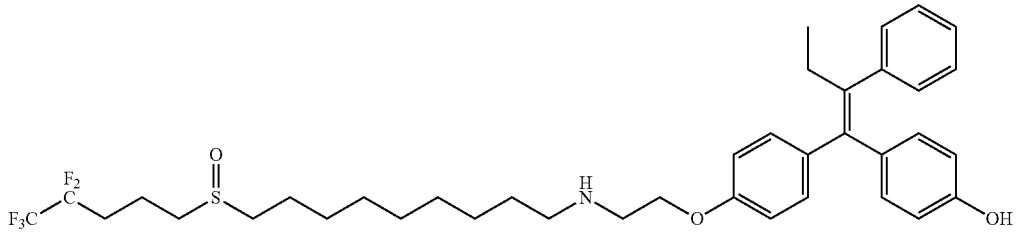

Example 14

(Z)-4-(1-(4-(2-(9-(4,4,5,5,5-pentafluoropentylsulfinyl) nonylamino)ethoxy)phenyl)-2-phenylbut-1-enyl)phenol phosphate ethyl carbamate

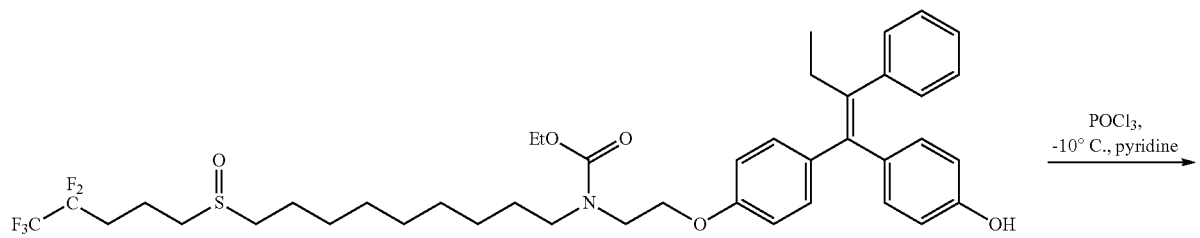

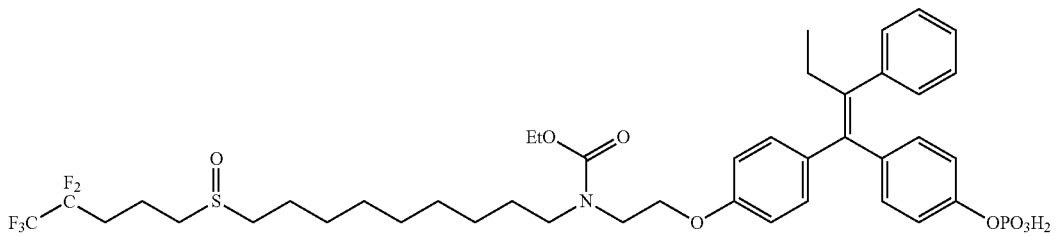

Phosphorous oxychloride (0.8-2 equiv) is added to dry pyridine (0.1-12 M/L) at −10 C. To this mixture is added gradually (E)-4-(1-(4-(2-(9-(4,4,5,5,5-pentafluoropentyl-sulfinyl)nonylamino)ethoxy)phenyl)-2-phenylbut-1-enyl) phenol ethyl carbamate (1 equiv). The mixture is stirred with cooling for 1-8 h and then allowed to warm slowly to room temperature and stirred at room temperature for 1-5 h. This reaction mixture is then added gradually to a mixture of 2-10% aqueous sodium bicarbonate and ice. The mixture is then allowed to stir for 1-5 h after which time, the pH of the mixture is slowly adjusted to ca. 2 using hydrochloric acid. At that time, a precipitate is formed. This mixture is filtered to yield the title compound among other products.

Example 15

The same sequence of reactions as described in reactions 1-5 above using 5-aminopentanol in step 1 to furnish (Z)-4-(1-(4-(2-(5-(4,4,5,5,5-pentafluoropentylsulfinyl)penty-lamino)ethoxy)phenyl)-2-phenylbut-1-enyl)phenol among other products.

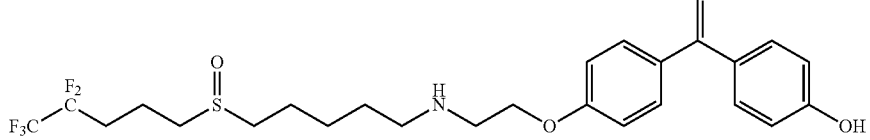

Example 16

The same sequence of reactions as described in reactions 1-5 above using 4-aminobutanol in step 1 to furnish (Z)-4-(1-(4-(2-(4-(4,4,5,5,5-pentafluoropentylsulfinyl)butylamino) ethoxy)phenyl)-2-phenylbut-1-enyl)phenol among other products.

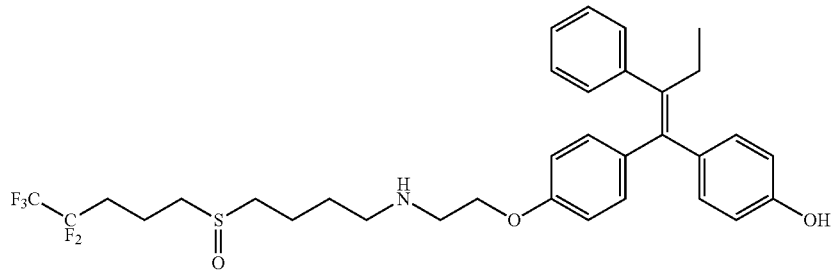

Example 17

The same sequence of reactions as described in reactions 1-5 above using 3-aminopropanol in step 1 to furnish (Z)-4-(1-(4-(2-(3-(4,4,5,5,5-pentafluoropentylsulfinyl)propy-lamino)ethoxy)phenyl)-2-phenylbut-1-enyl)phenol among other products.

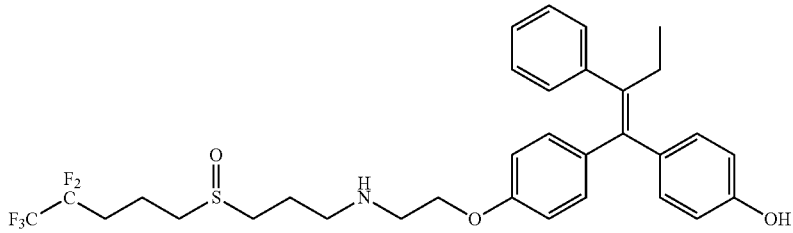

Example 18

The same sequence of reactions as described in reactions 1-5 above using 7-aminoheptanol in step 1 to furnish (Z)-4-(1-(4-(2-(7-(4,4,5,5,5-pentafluoropentylsulfinyl)heptylamino)ethoxy)phenyl)-2-phenylbut-1-enyl)phenol among other products.

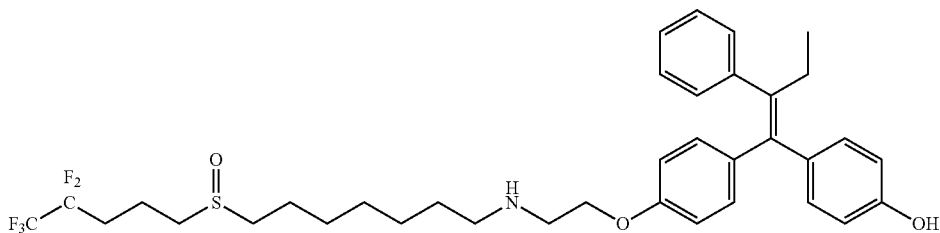

Example 19

The same sequence of reactions as described in reactions 1-5 above using 8-aminooctanol in step 1 to furnish (Z)-4-(1-(4-(2-(8-(4,4,5,5,5-pentafluoropentylsulfinyl)octylamino)ethoxy)phenyl)-2-phenylbut-1-enyl)phenol among other products.

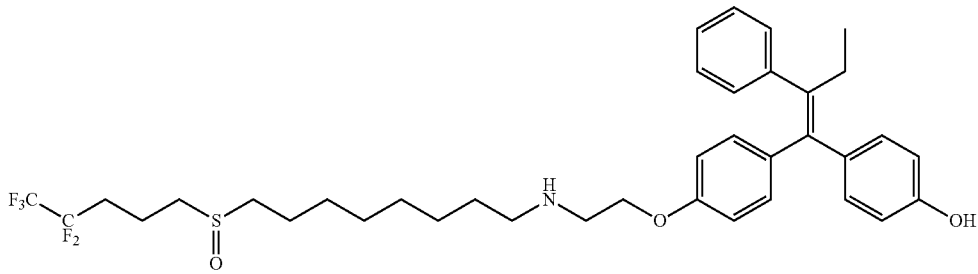

Example 20

The same sequence of reactions as described in reactions 1-5 above using 9-aminononanol in step 1 to furnish (Z)-4-(1-(4-(2-(9-(4,4,5,5,5-pentafluoropentylsulfinyl)nonylamino)ethoxy)phenyl)-2-phenylbut-1-enyl)phenol among other products.

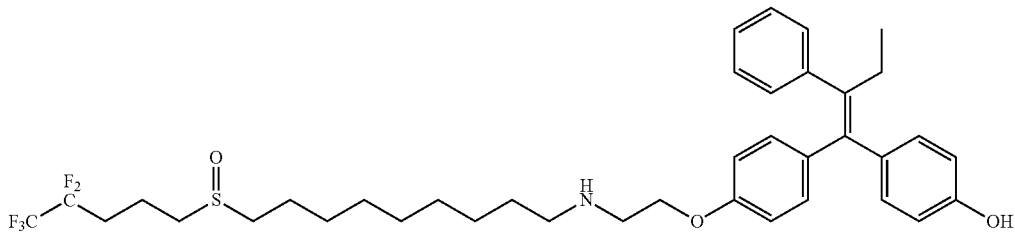

Example 21

(E)-4-(1-(4-(2-(9-(4,4,5,5,5-pentafluoropentylsulfi-
nyl) nonylamino)ethoxy)phenyl)-2-phenylbut-1-
enyl)phenol phosphate ethyl carbamate

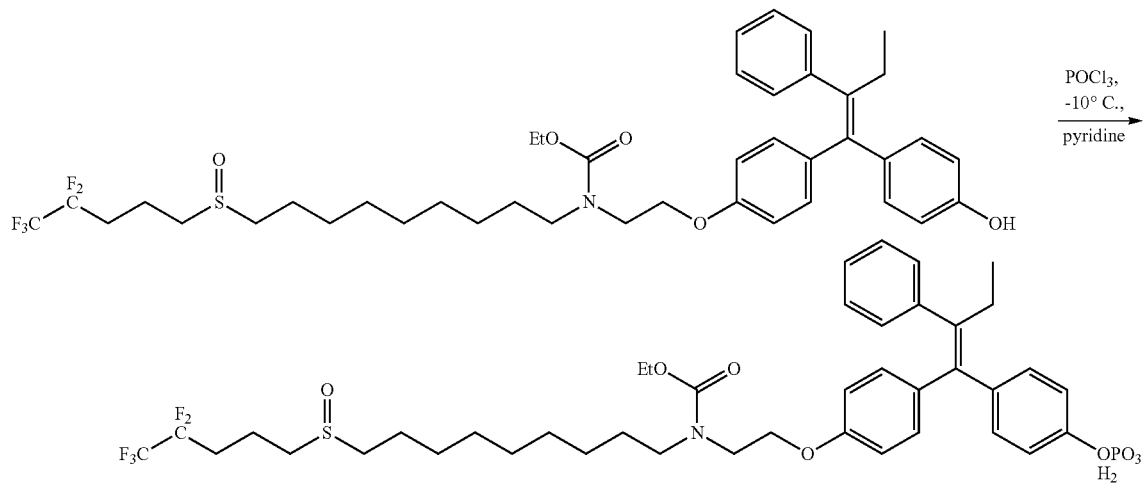

-continued

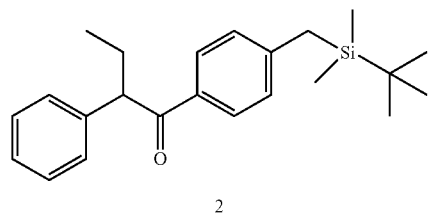

2

Phosphorous oxychloride (0.8-2 equiv) is added to dry pyridine (0.1-12 M/L) at −10 C. To this mixture is added gradually (Z)-4-(1-(4-(2-(9-(4,4,5,5,5-pentafluoropentyl-sulfinyl)nonylamino)ethoxy)phenyl)-2-phenylbut-1-enyl) phenol ethyl carbamate (1 equiv). The mixture is stirred with cooling for 1-8 h and then allowed to warm slowly to room temperature and stirred at room temperature for 1-5 h. This reaction mixture is then added gradually to a mixture of 2-10% aqueous sodium bicarbonate and ice. The mixture is then allowed to stir for 1-5 h after which time, the pH of the mixture is slowly adjusted to ca. 2 using hydrochloric acid. At that time, a precipitate is formed. This mixture is filtered to yield the title compound among other products.

Example 22

Ketone 2

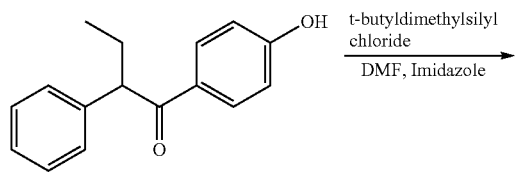

Phenol 1 (10 g, 0.041 moles) was dissolved in dry DMF (40 ml) at room temperature under $N_2$. Imidazole (5.67 g, 0.083 moles) was added followed by tert-butyldimethylsilyl chloride (6.91 g, 0.0458 moles). The reaction was stirred for 2 hours, added to saturated sodium chloride solution (200 ml) and extracted with ethyl acetate (250 ml). The ethyl acetate layer was separated, washed 3 times with NaCl solution (100 ml), separated, dried over sodium sulfate, filtered through a small pad of silica gel with the aid of ethyl acetate, and concentrated to give 14 grams (95%) of a brown viscous oil containing ketone 2 among other products. A TLC system of ethyl acetate/hexanes (3:7) was used to follow the progress of the reaction.

Example 23

Adduct 3

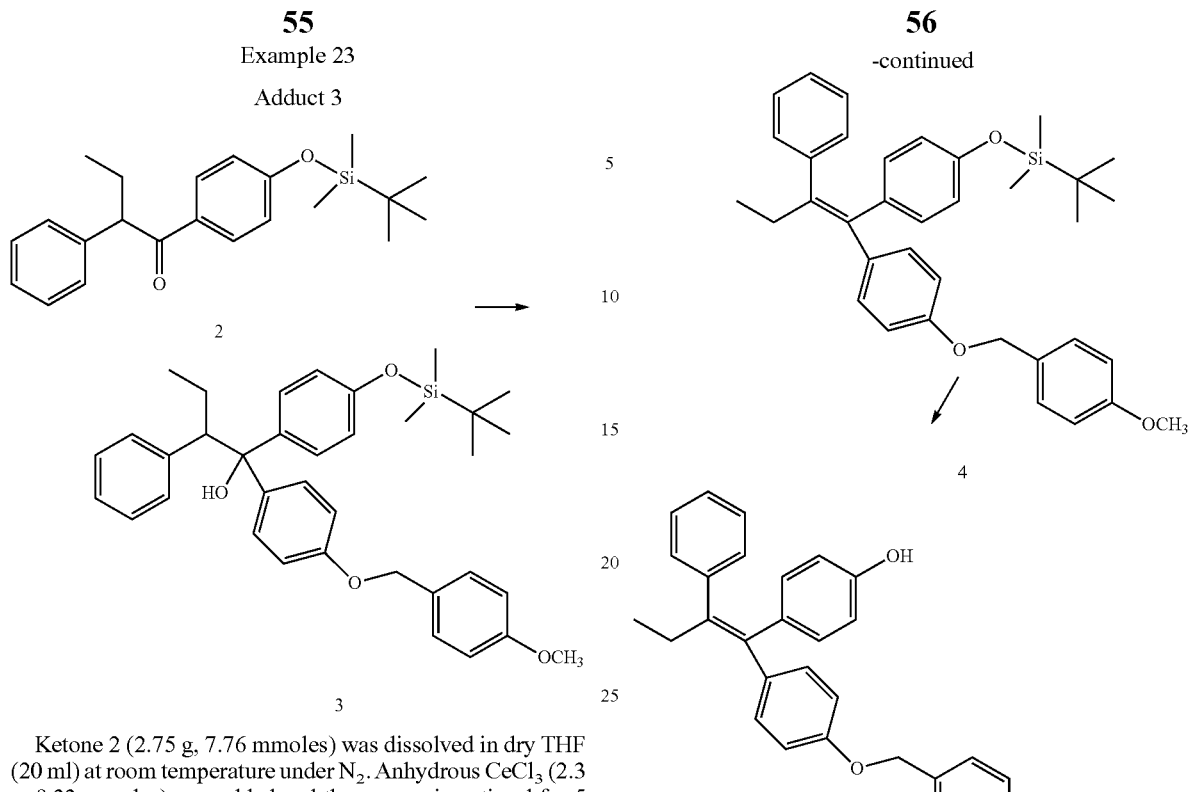

Ketone 2 (2.75 g, 7.76 mmoles) was dissolved in dry THF (20 ml) at room temperature under $N_2$. Anhydrous $CeCl_3$ (2.3 g, 9.33 mmoles) was added and the suspension stirred for 5 hours. 4-Bromophenol-p-methoxybenzyl ether (2.73 g, 9.32 mmoles) was dissolved in dry THF (35 ml) in a separate flask and cooled to −78° C. (forming a paste at this temperature) under $N_2$. Addition of n-butyllithium (3.73 ml, 2.5M in hexanes, 9.32 mmoles) dropwise in 10 minutes to 4-Bromophenol-p-methoxybenzyl ether gave a homogeneous solution which was stirred for 40 minutes. This solution was added via cannula to the $CeCl_3$-ketone 2 suspension which had been cooled to −10° C. The reaction mixture was allowed to warm to rt and stirred for 16 hours. The reaction was quenched with 1N aqueous HCl solution and extracted with MTBE (2×100 ml). The organic layer was separated, dried over sodium sulfate, filtered, concentrated, and purified by flash chromatography. Purification using ethyl acetate/hexanes gave 2.55 g (58%) of a light yellow foam containing adduct 3 among other products.

Example 24

Phenol 5

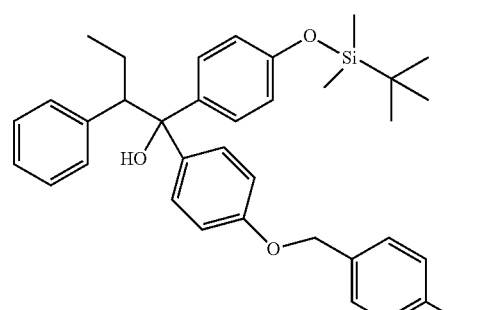

Adduct 3 (2.3 g, 4.05 mmoles) was dissolved in ethanol (25 ml) at rt. PPTS (0.31 g, 1.19 mmoles) was added and the reaction stirred for 17 hours at rt giving predominantly a mixture of (55:45) E/Z olefins with the tert-butyldimethyl silyl group still attached. Ethanol was evaporated and the crude redissolved in dry THF (20 ml). Tetra-n-butyl ammonium fluoride solution (1M in THF, 8.1 mmoles) was added. The reaction was stirred for 1 hour at room temperature, the THF evaporated, and the crude purified by flash silica chromatography using ethyl acetate/hexanes to give 1.7 g (93%) of phenol 5 as a light yellow viscous oil containing E and Z isomers among other products.

Example 25

Ether 6

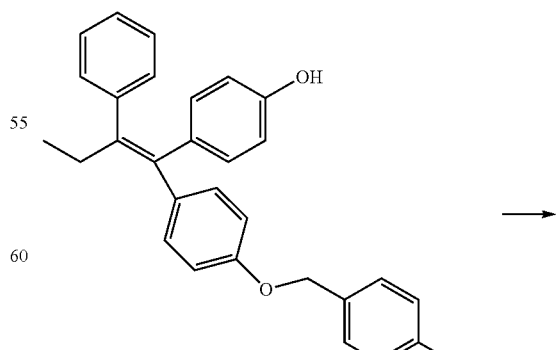

-continued

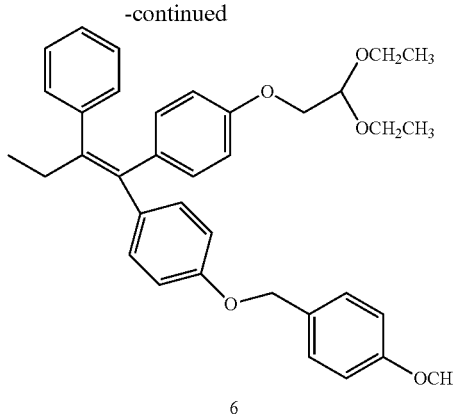

6

Phenol 5 (1.69 g, 3.87 mmoles) was dissolved in dry DMF (14 ml). The solution was cooled to 0° C. under $N_2$ and NaH (0.193 g, 4.82 mmoles) was added. After 30 minutes, bromoacetaldehyde diethyl acetal (0.80 g, 4.06 mmoles) was added and the reaction mixture heated at 55° C. for 20 hours. The reaction was cooled, added to saturated NaCl solution (50 ml), and extracted with ethyl acetate (75 ml). The organic layer was separated, washed 3 times with saturated NaCl solution (50 ml), dried over sodium sulfate, filtered, and concentrated. Purification by flash chromatography using ethyl acetate/hexanes gave 1.86 g (87%) of ether 6 as a light yellow oil containing E and Z isomers among other products.

Example 26

Phenol 7

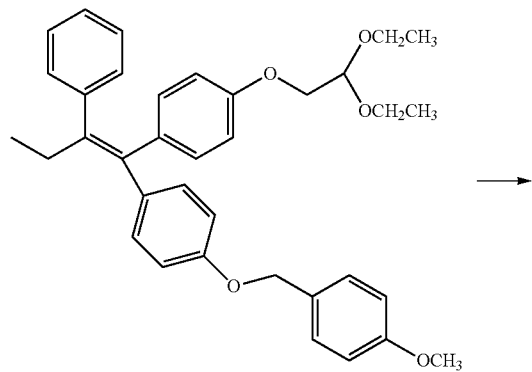

6

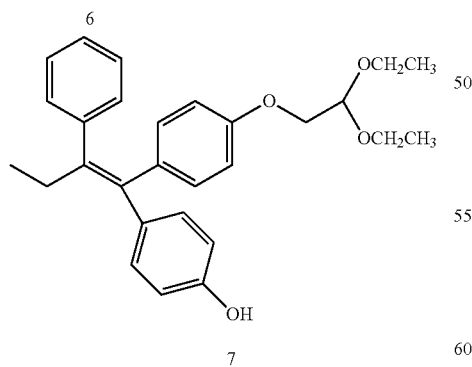

7

To ether 6 (2.0 g, 3.62 mmoles) dissolved in dry methanol (90 ml) was added 0.3 g of camphorsulfonic acid. The reaction was heated at reflux for 16 hours, cooled, and concentrated. The crude was partitioned between ethyl acetate (50 ml) and water (50 ml), the organic layer separated, dried over sodium sulfate, filtered, and evaporated. Purification by flash chromatography using ether/hexanes gave 1.50 grams (approx 100%) of phenol 7 as a light yellow oil containing E and Z isomers among other products.

Example 27

Aldehyde 8

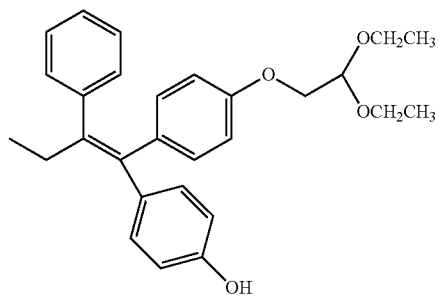

7

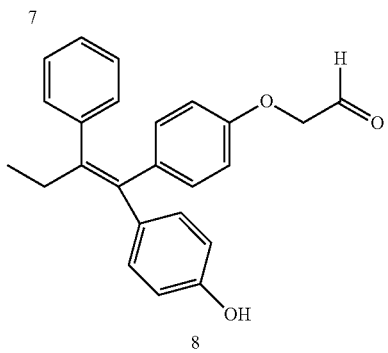

8

Phenol 7 (1.69 g, 4.18 mmoles, calculated for dimethyl acetal) was dissolved in THF (18 ml) at room temperature. 3M HCl (18 ml) was added. The reaction was heated at 50° C. for 17 hours. After cooling, the reaction mixture was added to ethyl acetate (50 ml), the organic layer separated, dried over sodium sulfate, filtered and concentrated to give 1.59 g of crude aldehyde 8 containing E and Z isomers among other products.

Example 28

Endoxifen (9)

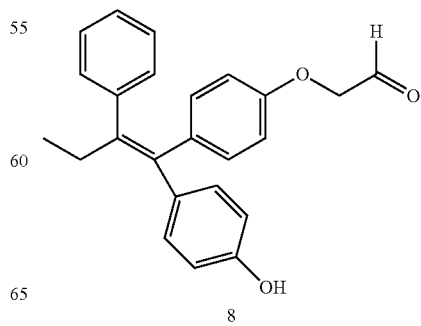

8

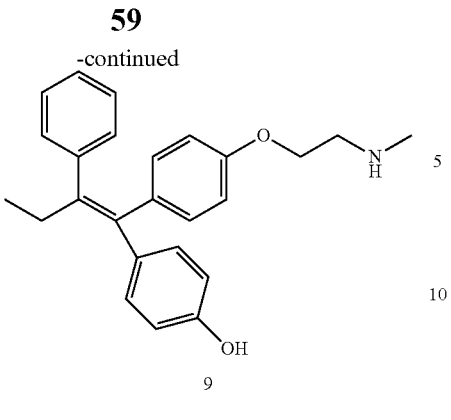

9

Aldehyde 8 (0.872 g, 2.43 mmoles) was dissolved in dry THF (6 ml) at room temperature. MgSO₄ (6 g) was added, followed by methylamine (2.67 ml, 5.34 mmoles, 2.0M solution in THF). The reaction was stirred for 16 hours, filtered, and concentrated. The crude imine was redissolved in anhydrous ethanol (20 cc) and the solution cooled to 0° C. NaBH₄ (0.11 g) was added portionwise, the reaction mixture stirred for 1 hour with warming to rt. Water was added and the mixture was extracted with ethyl acetate (50 ml). The organic layer was separated, dried over sodium sulfate, filtered, and concentrated. The crude product was purified by flash chromatography using CH₂Cl₂/methanol/aqueous NH₃ and to yield 0.150 g of a light pink foam containing an (E/Z) mixture of endoxifen (9).

Examples 28a Through 28f

Analogs of endoxifen can be prepared according to the procedure of Example 28, where methylamine is replaced as follows:

| Example | Amine |
|---------|-----------|
| 28a | ethylamine |
| 28b | propylamine |
| 28c | butylamine |
| 28d | pentylamine |
| 28e | hexylamine |
| 28f | heptylamine |

Example 29

Ester 10

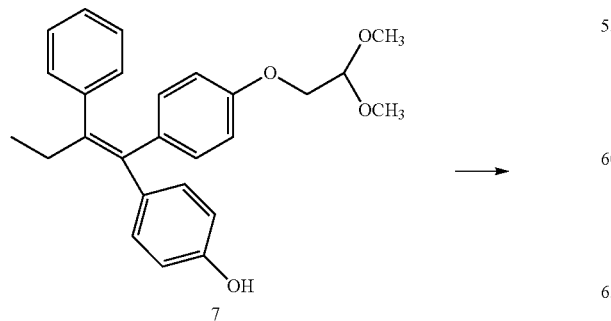

7

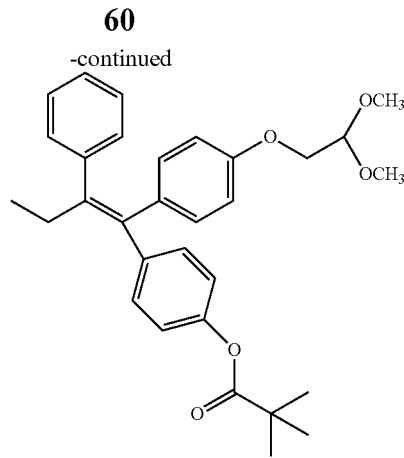

10

Phenol 7 (0.414 g, 1.02 mmoles) and dimethylaminopyridine (0.226, 1.85 mmoles) was dissolved in dry dichloromethane (10 ml) and the solution cooled to 0° C. under N₂. Pivaloyl chloride (0.21 g, 1.73 mmoles) was added dropwise via syringe and the reaction was then allowed to warm to room temperature. After 6 hours, 1N aqueous HCl was added and additional dichloromethane (50 ml) was added. The organic layer was separated, dried over Na₂SO₄, filtered, and concentrated. Purification by flash chromatography using ethyl acetate/hexanes gave 0.32 grams of ester 10 as a light yellow oil containing E and Z isomers among other products.

Example 30

Aldehyde 11

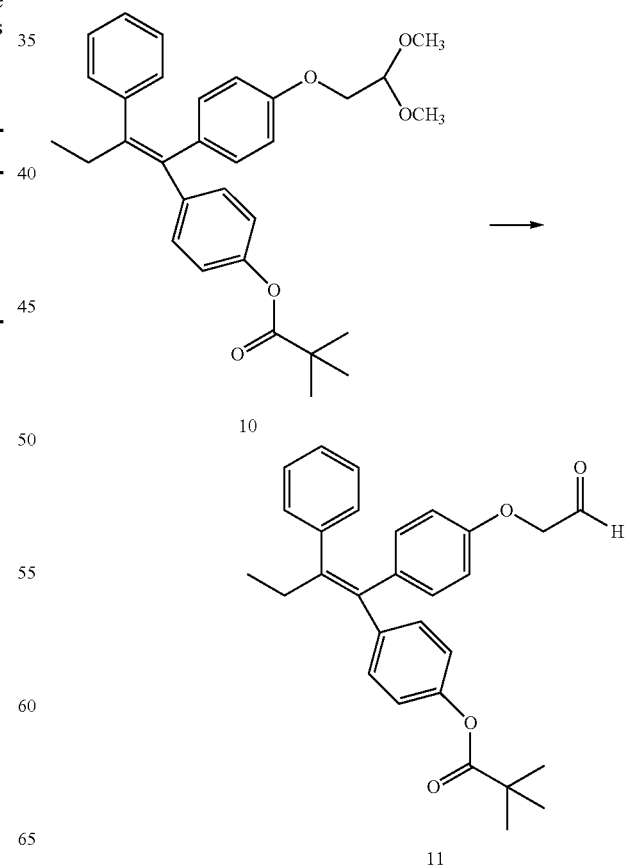

Dimethyl acetal 10 (0.32 g, 0.63 mmoles) was dissolved in 10 ml of THF at room temperature. 6 ml of 3N HCl was added and the reaction mixture heated at 45-50° C. for 15 hours. After cooling, the mixture was added to water and ethyl acetate (1:1, 50 ml). The organic layer was separated, dried over Na$_2$SO$_4$, filtered, and concentrated to give 0.23 grams of crude aldehyde 11 as a light yellow oil containing E and Z isomers among other products.

Example 31

Pivalate Ester 12

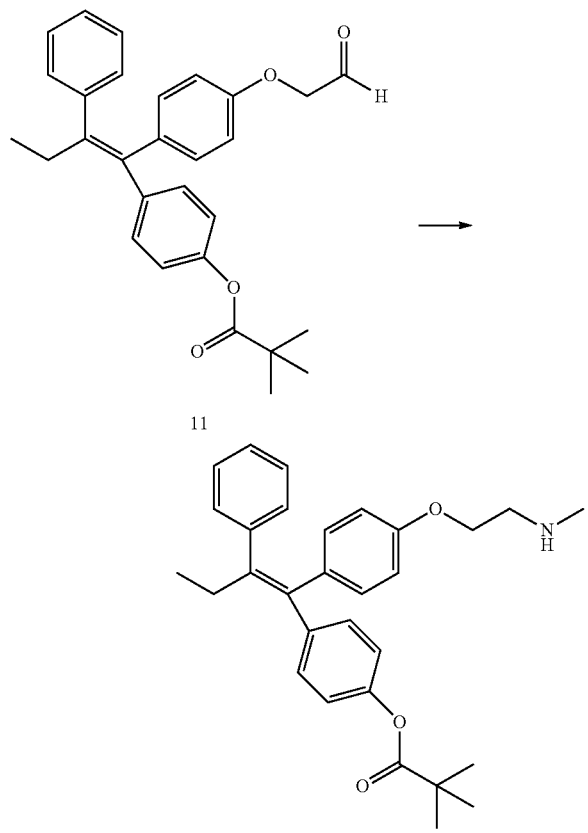

Aldehyde 11 (0.273 g, 0.52 mmoles) was dissolved in dry THF (10 ml) at rt. MgSO$_4$ (1.33 g) was added, followed by methylamine (0.52 ml, 1.04 mmoles, 2.0M solution in THF). The reaction was stirred for 16 hours, filtered, and concentrated. The crude imine was redissolved in anhydrous ethanol (10 cc) and the solution cooled to 0° C. NaBH$_4$ (0.02 g) was added, the reaction mixture stirred for 1 hour with warming to rt. Water was added and the mixture extracted with ethyl acetate (20 ml). The organic layer was separated, dried over sodium sulfate, filtered, and concentrated. The crude product was purified by flash chromatography using CH$_2$Cl$_2$/methanol/aqueous NH$_3$ and gave 0.07 g of pivalate ester 12 as a light pink oil containing a mixture (E/Z) isomers among other products.

Example 32

Ester 13

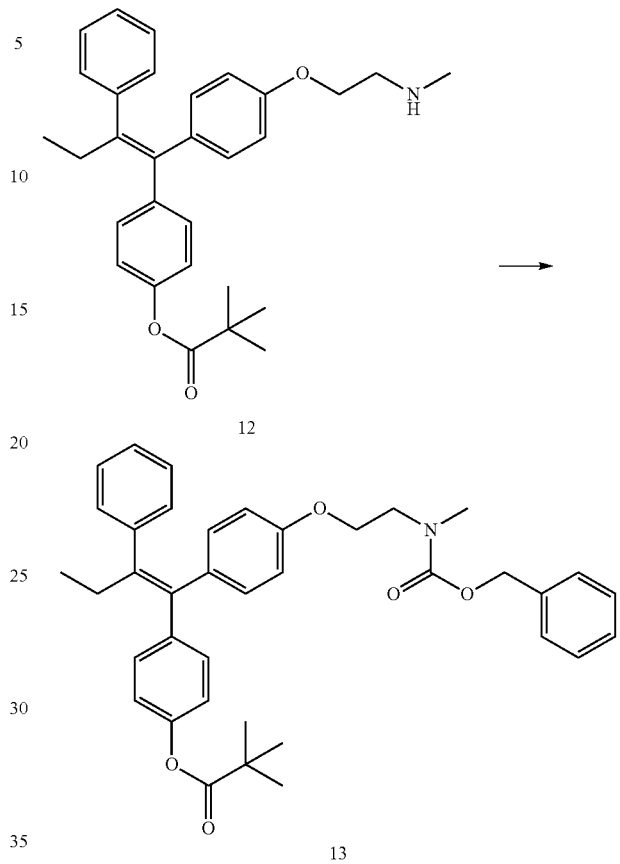

Pivalate ester 12 (E/Z mixture) (0.059 g, 0.128 mmoles) was dissolved in 1 ml of THF. Aqueous NaOH (2M, 96 µl) was added and the reaction mixture cooled to 0° C. Benzyl chloroformate (0.033 g, 0.19 mmoles) was added. The reaction was allowed to warm to rt and, when determined to be complete by tlc, added to water (10 ml) and extracted with ethyl acetate (20 ml). The organic layer was washed with saturated aqueous sodium bicarbonate solution, separated, dried over MgSO$_4$, filtered through a small pad of silica with the aid of ethyl acetate and concentrated to give 81 mg of a light yellow oil 13. Crude 13 was used without further purification.

Example 33

Compound 14

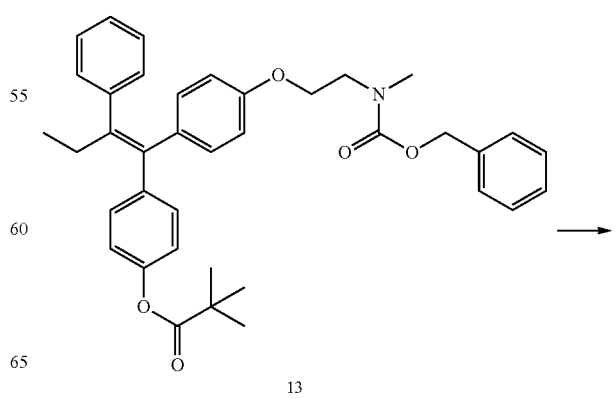

-continued

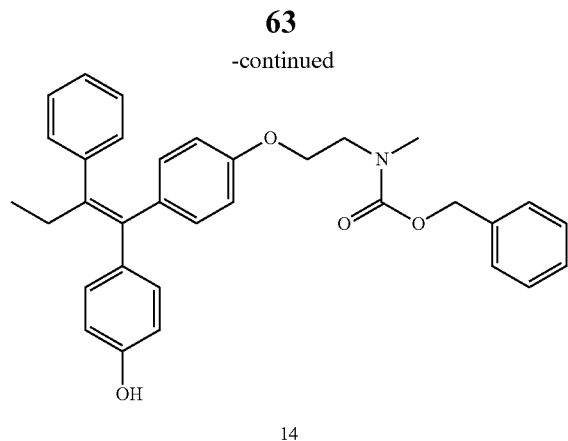

14

Carbamate 13 (0.081 g, 0.13 mmoles) was dissolved in 4 ml of dry THF. The solution was cooled to 0° C. under $N_2$. LiAlH$_4$ (0.026 g, 0.70 mmoles) was added. The reaction mixture was stirred for 30 minutes and then water (39 μl) added. The mixture was filtered through celite with the aid of THF (15 ml) and ethyl acetate (15 ml). The filtrate was dried over MgSO$_4$, filtered, and concentrated to give 45 mg of 14.

Example 34

Compound 15

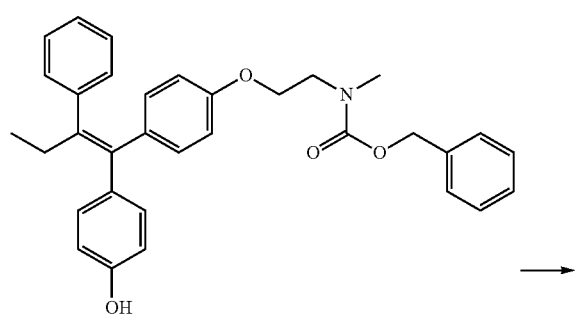

14

→

-continued

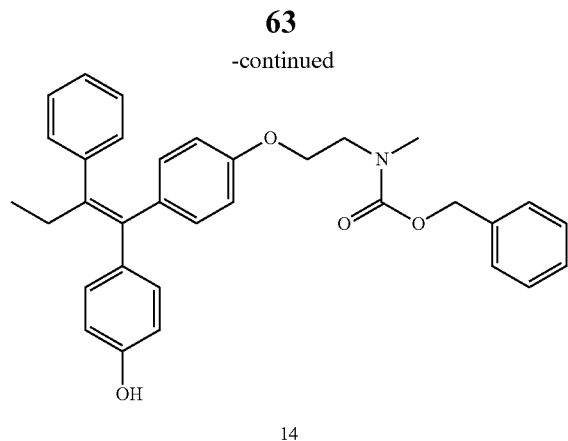

15

Phenol 14 was dried prior to reaction by treatment with 3×10 ml of dry acetonitrile followed by rotary evaporation. The phenol 14 (0.045 g, 0.087 mmoles) was then dissolved in dry acetonitrile (1.5 ml) and then cooled to −10° C. under $N_2$. CCl$_4$ (0.068 g, 0.44 mmoles) was added and the suspension stirred for 10 minutes. Hunig's base (0.024 g, 0.18 mmoles) and N,N-dimethylaminopyridine (1 mg) were added. After 1 minute, dibenzyl phosphate (0.034 g, 0.12 mmoles) was added. Stirring was continued for 1 hour and 15 minutes, then aqueous KH$_2$PO$_4$ solution (1 ml, 0.5M) was added, the mixture warmed to rt and extracted with ethyl acetate (25 ml). The organic layer was separated, dried over Na$_2$SO$_4$, filtered, and concentrated to give crude 15. Purification by flash chromatography using dichloromethane/methanol 9:1 gave 20 mg of 15.

Example 35

Compound 16

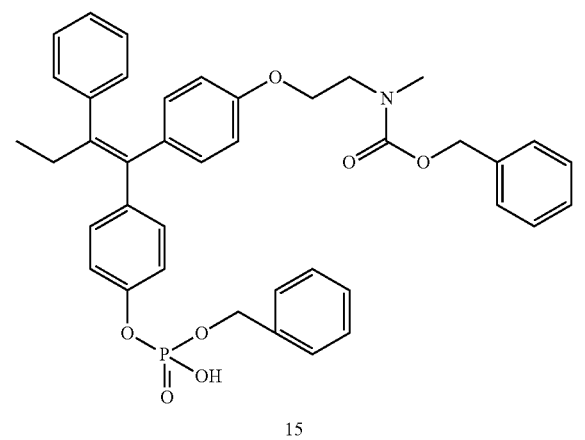

Phosphate 15 (0.040 g, 0.052 mmoles) is dissolved in 20 ml of ethanol. Pd on carbon (10%, 30 mg) is added. The mixture is hydrogenated at rt and 40 psi for 5 hours. The catalyst is removed by filtration through celite and the filtrate concentrated to give 16.

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described therein will become apparent to those skilled in the art from the foregoing description. Such modifications are also intended to fall within the scope of the appended claims. All publications cited herein are incorporated by reference in their entirety.

The invention claimed is:

1. A compound of formula I or formula II:

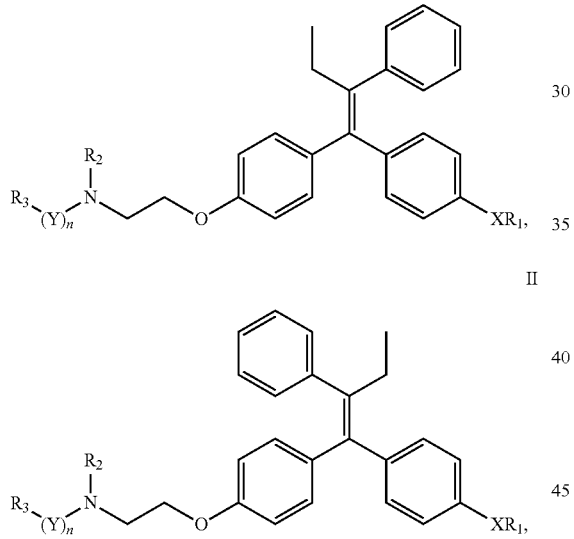

and pharmaceutically acceptable salts thereof, wherein
X is H, O or S;
$R_1$ is H, or if X is O, $XR_1$ is independently selected from the group consisting of alkyl esters, phosphate esters, diphosphate esters, and triphosphate esters, or not present when X is H;
$R_2$ is H, $CH_3$, a lower alkyl group, a divalent cyclic alkyl group forming a quaternary ammonium, an amide, a carbamate, an N-acyloxyalkyl group, an N-acylalkoxy carbonyl group, a beta-aminoketone, a (oxodioxolenyl) methyl group, an N-Mannich base, an imine (Schiff base), an enamine, an enaminone, an azo compound, THTT or PEG;
$R_3$ is selected from a $C_1$-$C_6$ perfluoroalkyl group;
n is an integer from 1 to 10; and
Y is a linker.

2. A compound according to claim 1, wherein $R_3$ is selected from perfluoromethyl and perfluoroethyl.

3. A compound of formula I or formula II:

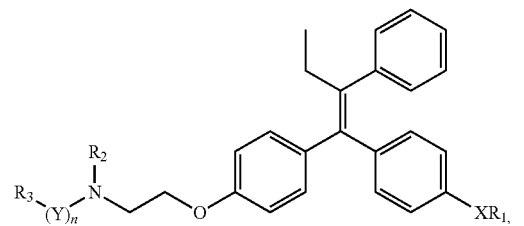

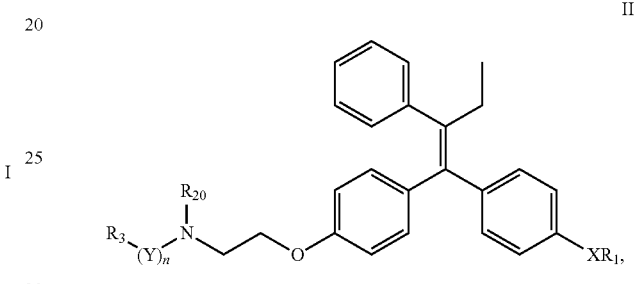

and pharmaceutically acceptable salts thereof, wherein
X is H, O or S;
$R_1$ is H, or if X is O, $XR_1$ is independently selected from the group consisting of alkyl esters, phosphate esters, diphosphate esters, and triphosphate esters, or not present when X is H;
$R_2$ is H, $CH_3$, a lower alkyl group, a divalent cyclic alkyl group forming a quaternary ammonium, an amide, a carbamate, an N-acyloxyalkyl group, an N-acylalkoxy carbonyl group, a beta-aminoketone, a (oxodioxolenyl) methyl group, an N-Mannich base, an imine (Schiff base), an enamine, an enaminone, an azo compound, THTT or PEG;
$R_3$ is a polyfluoro alkyl group;
n is an integer from 1 to 10; and
Y is —$R_4SR_5$—, —$R_4SOR_5$—, —$R_4SO_2R_5$—, —$R_4OR_5$—, —$R_4NR_2R_5$—, —$R_4NR_2COR_5$—, —$R_4CONR_2R_5$—, —$R_4COR_5$—, —$R_4C(=O)OR_5$—, —$R_4OC(=O)R_5$—, —$R_4POR_5$—, —$R_4OP(=O)(OH)OR_5$—, —$R_4NR_2C(=NR_2)NR_2R_5$—, —$R_4NR_2C(=O)NR_2R_5$—, —$R_4NR_2C(=O)OR_5$—, and —$R_4OC(=O)NR_2R_5$—;
wherein $R_2$ is as defined above, and $R_4$ and $R_5$ are independently selected from $C_1$-$C_{10}$ straight-chain, branched, or cyclic alkyl, $C_2$-$C_{10}$ straight-chain, branched, or cyclic alkenyl, $C_2$-$C_{10}$ straight-chain or branched alkynyl, divalent aryl, and divalent heterocyclyl groups.

4. A compound according to claim 3, wherein Y is —$R_4OR_5$— or —$R_4NR_2R_5$—.

5. A compound according to claim 4, wherein n is an integer from 2 to 4.

6. A compound selected from the group consisting of
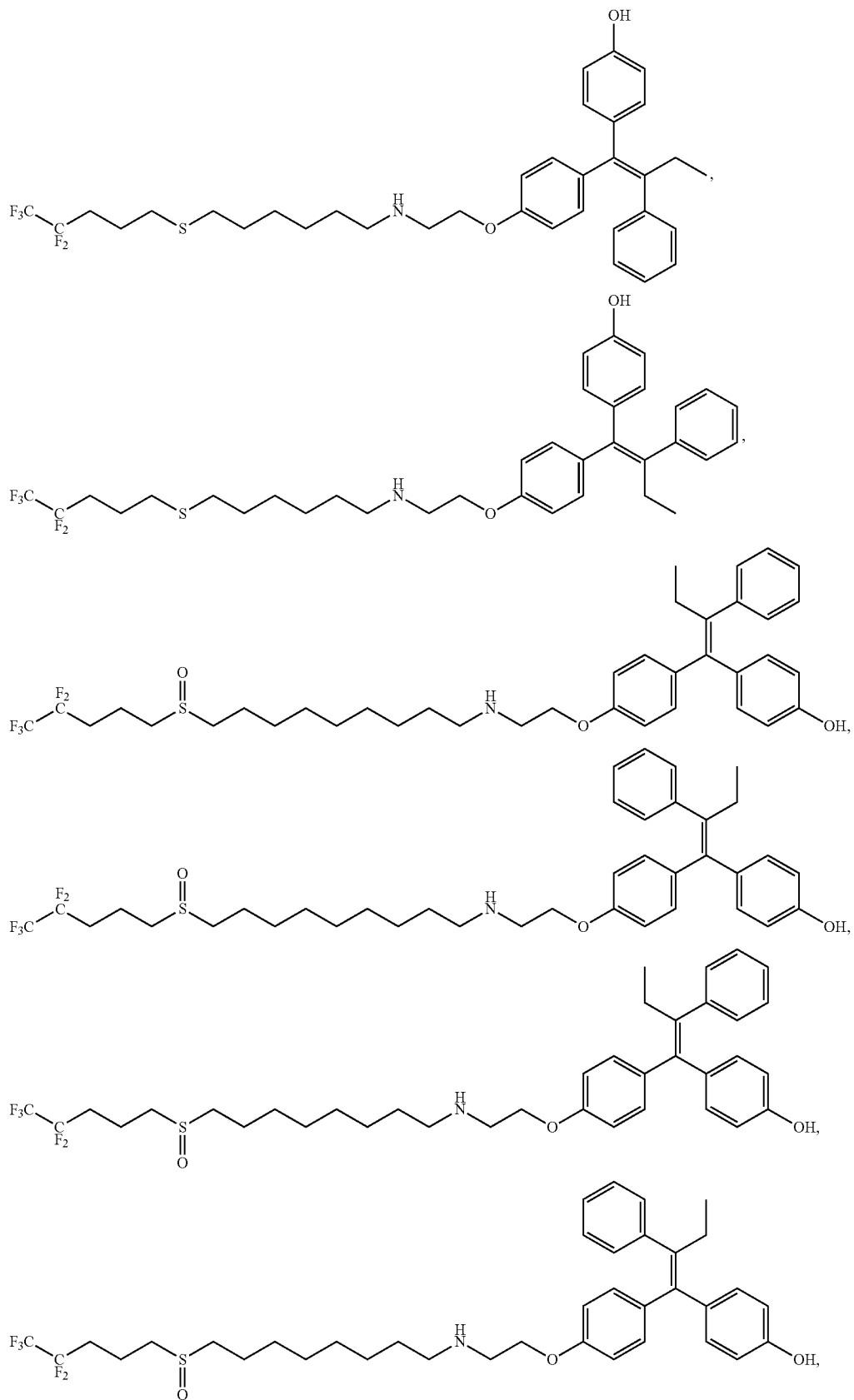

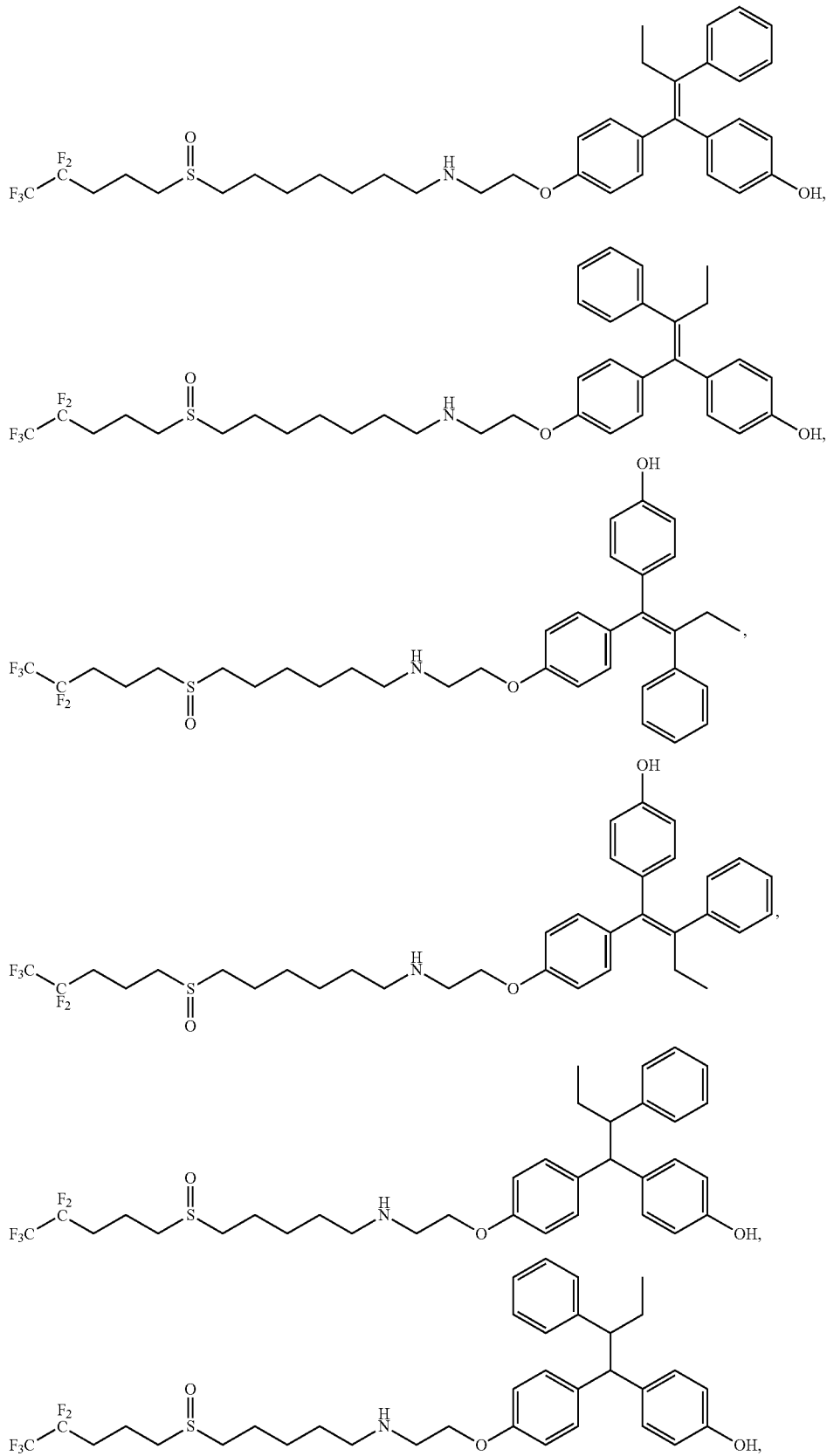

-continued

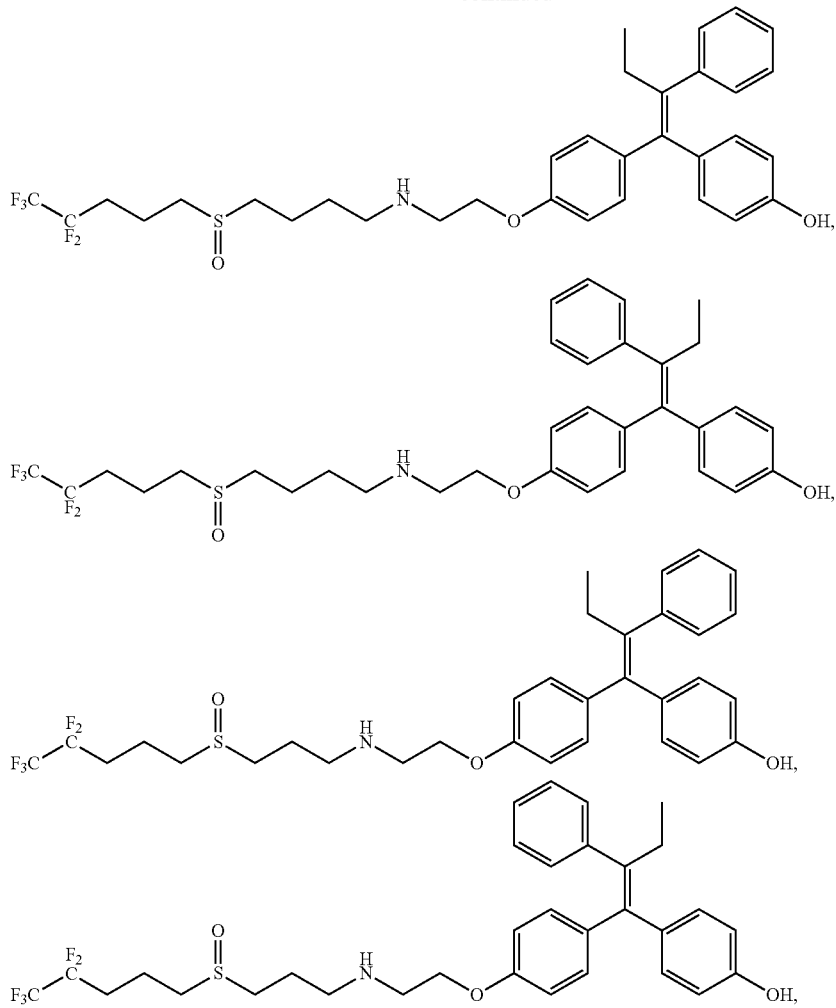

7. A composition comprising a compound according to claim 1 and a pharmaceutically acceptable carrier.

8. A composition according to claim 7, wherein the compound is optically active, and wherein the composition further comprises an enantiomer of said compound, and further wherein the compound and its enantiomer are present in an equimolar ratio.

9. A composition comprising a compound of claim 1, which compound is in a form selected from the group consisting of an anhydrous form, a single crystalline form, a mixture of polymorphic forms, and mixtures thereof.

10. A composition comprising a mixture of compounds according to claim 1, wherein the mixture comprises a compound according to Formula I and a compound according to Formula II, wherein said compounds are E/Z isomers of each other.

11. A composition according to claim 10, wherein the E/Z isomers are present in an equimolar ratio.

12. A method of treating breast cancer in a human in need thereof comprising administering a compound according to claim 1 to a human.

13. A method according to claim 12, wherein the human is female.

14. A method according to claim 13, wherein the female exhibits reduced metabolism of tamoxifen.

15. The method according to claim 12, further comprising administration of one or more anti-cancer agents.

16. The method according to claim 12, wherein the breast cancer is ER-positive.

17. A method of reducing the risk of recurrence of breast cancer in a human previously treated for breast cancer comprising administering a compound according to claim 1 to said human.

* * * * *